US011414451B2

(12) United States Patent
Kotala et al.

(10) Patent No.: US 11,414,451 B2
(45) Date of Patent: Aug. 16, 2022

(54) FLOXURIDINE SYNTHESIS

(71) Applicant: NuCana plc, Edinburgh (GB)

(72) Inventors: Mani Bushan Kotala, Mandal (IN); Venkata Lakshmi Narasimha Rao Dammalapati, Hyderabad (IN)

(73) Assignee: NuCana plc, Edinburgh (GB)

( * ) Notice: Subject to any disclaimer, the term of this patent is extended or adjusted under 35 U.S.C. 154(b) by 181 days.

(21) Appl. No.: 16/647,592

(22) PCT Filed: Sep. 18, 2018

(86) PCT No.: PCT/GB2018/052662
§ 371 (c)(1),
(2) Date: Mar. 16, 2020

(87) PCT Pub. No.: WO2019/053476
PCT Pub. Date: Mar. 21, 2019

(65) Prior Publication Data
US 2020/0262859 A1    Aug. 20, 2020

(30) Foreign Application Priority Data

Sep. 18, 2017 (GB) .................... 1715011

(51) Int. Cl.
*C07H 1/00* (2006.01)
*C07H 19/06* (2006.01)
*C07H 19/073* (2006.01)
*C07H 19/10* (2006.01)

(52) U.S. Cl.
CPC .............. *C07H 19/06* (2013.01); *C07H 1/00* (2013.01); *C07H 19/073* (2013.01); *C07H 19/10* (2013.01)

(58) Field of Classification Search
None
See application file for complete search history.

(56) References Cited

U.S. PATENT DOCUMENTS

| 2,802,005 | A | 8/1957 | Heidelberger et al. |
| 2,945,038 | A | 7/1960 | Duschinsky et al. |
| 3,201,387 | A | 8/1965 | Heidelberger et al. |
| 7,601,820 | B2 | 10/2009 | Wang et al. |
| 8,492,539 | B2 | 7/2013 | Chun et al. |
| 8,629,263 | B2 | 1/2014 | Ross et al. |
| 8,735,569 | B2 | 5/2014 | Ross et al. |
| 8,871,737 | B2 | 10/2014 | Smith et al. |
| 8,933,053 | B2 * | 1/2015 | McGuigan ............... A61P 35/02 514/51 |
| 9,090,642 | B2 | 7/2015 | Cho et al. |
| 9,221,866 | B2 | 12/2015 | McGuigan et al. |
| 9,278,990 | B2 | 3/2016 | Smith et al. |
| 9,655,915 | B2 | 5/2017 | McGuigan et al. |
| 10,022,390 | B2 | 7/2018 | McGuigan et al. |
| 10,117,888 | B2 | 11/2018 | Griffith et al. |
| 10,786,523 | B2 | 9/2020 | Griffith et al. |
| 11,040,051 | B2 | 6/2021 | Griffith et al. |
| 2003/0109697 | A1 | 1/2003 | Shepard |
| 2010/0249068 | A1 | 9/2010 | Beigelman et al. |
| 2013/0252918 | A1 | 1/2013 | McGuigan |
| 2019/0374564 | A1 | 12/2019 | Griffith et al. |
| 2019/0375778 | A1 | 12/2019 | Griffith et al. |
| 2020/0181186 | A1 | 6/2020 | Griffith et al. |
| 2020/0262859 | A1 | 8/2020 | Kotala et al. |

FOREIGN PATENT DOCUMENTS

| GB | 1377027 A | 12/1994 |
| JP | S54151987 A | 11/1979 |
| WO | WO 2002/068443 A1 | 9/2002 |
| WO | WO 2005/012327 A2 | 2/2005 |
| WO | WO 2006/063149 A1 | 6/2006 |
| WO | WO 2006/100439 A1 | 9/2006 |
| WO | WO 2007/056596 A1 | 5/2007 |
| WO | WO 2008/121634 A2 | 10/2008 |
| WO | WO 2010/081082 A2 | 7/2010 |
| WO | WO-2012/117246 A1 | 9/2012 |

OTHER PUBLICATIONS

Lagerwall et al., Tetrahedron Letters, 56(43), pp. 5950-5953, 2015. (Year: 2015).*
Aayoma et al., "Synthesis of 5-Fluoro-2'-deoxy-β-uridine," The Chemical Society of Japan, 12: 1765-1770 (1986).
International Search Report and Written Opinion for International Application No. PCT/GB2018/052662 dated Nov. 22, 2018.
Lagerwall et al., "Temperature controlled stereoselectivity in the synthesis of 5-halo-2'-deoxyuridine derivatives," Tetrahedron Letters, 56(43): 5950-5953 (2015).
Noyori et al., "Condensation of 1-Fluorofuranoses and Silylated Nucleobases Catalyzed by Tetrafluorosilane#," Chemistry Letters, 16(1): 57-60 (1987).
Okajchi et al., "Stereoselective Synthesis of alpa-Deoxyribonucleosides from 1-O-Acetyl-3-O-[2-(methylsulfinyl)ethyl]-2-deoxribose," Chemistry Letters, 18(5): 801-804 (1989).
United Kingdom Search Report for International Application No. GB1715011.1 dated Jun. 1, 2018.
Yang et al., "A dramatic concentration effect on the stereoselectivity of N-glycosylation for the synthesis of 2'deoxy-β-ribonucleosides," ChemComm, 48(56): 7097-7099 (2012).
U.S. Pat. No. 10,993,957, B2, U.S. Appl. No. 16/021,103, McGuigan et al., May 4, 2021.
2018/0369266, A1, U.S. Appl. No. 16/065,402, Kennovin et al., Dec. 27, 2018.
2020/0345755, A1, U.S. Appl. No. 16/642,835, Griffith, Nov. 5, 2020.
2022/0023330, A1, U.S. Appl. No. 17/223,241, McGuigan et al., Jan. 27, 2022.
2022/0031728, A1, U.S. Appl. No. 17/231,606, Kennovin et al., Feb. 3, 2022.
Abraham et al.; "Synthesis and Biological Activity of Aromatic Amino Acid Phosphoramidates of 5-Fuoro-2'-deoxyuridine and 1-beta-Arabinofuranosylcytosine: Evidence of Phosphoramidase Activity," J Med Chem, 1996, 39:4569-4575.

(Continued)

*Primary Examiner* — Traviss C Mcintosh, III
(74) *Attorney, Agent, or Firm* — Knowles Intellectual Property Strategies, LLC

(57) ABSTRACT

The present invention relates to a process for the preparation of floxuridine. Floxuridine may be useful as an anti-cancer drug. Floxuridine may also be useful in the preparation of other anti-cancer drugs, e.g. NUC-3373.

32 Claims, No Drawings

(56) References Cited

OTHER PUBLICATIONS

Blanka Gönczy "Design, Synthesis and Biological Evaluation of Nucleotide Pro-drugs Centred on Clinically Active Anticancer Nucleosides," Thesis of Cardiff School of Pharmacy and Pharmaceutical Sciences Cardiff University; 2016.

Congiatu, Costantino "Design, Synthesis and Biological Evaluation of Some Noel Nucleotide Prodrugs as Potential Anticancer Agents," Thesis submitted to the University of Wales for the Degree of Philosophiae Doctor, The Welsch School of Pharmacy University of Wales Cardiff, Feb. 2006.

Ebenryter-Olbinska, Katarzyna et al. "Efficient synthesis of 2'-deoxyzebularine and its α-anomer by the silyl method of N-glycosylation. Crystal structures and conformational study in solution," Carbohydrate Research, vol. 392, Jun. 17, 2014, pp. 7-15.

Ferrari, Valentina "Synthesis and Biological Evaluation of Novel Nucleosides and Nucleotides as Potential Therapeutic Agents," Thesis Cardiff University, Sep. 2015.

Liu, Zhaogui et al. "Highly stereoselective synthesis of 2'-deoxy-β-ribonucleosides via a 3'-(N-acetyl)-glycyl-directing group," Tetrahedron Letters, vol. 51, Issue 2, Jan. 13, 2010, pp. 240-243.

McGuigan, C. et al. "Phosphoramidate ProTides of the anticancer agent FUDR successfully deliver the preformed bioactive monophosphate in cells and confer advantage over the parent nucleoside," Journal of Medicinal Chemistry vol. 54, No. 20 pp. 7247-7258 (2011).

Mehellou, Y. et al. "Phosphoramidates of 2'-B-d-arabinouridine (AraU) as phosphate prodrugs: design, synthesis, in vitro activity and metabolism," Bioorg. Med. Chem. 2010, 18, 2439.

Murziani, Paola "Anticancer Drug Design and Synthesis," Thesis submitted to the Welsh School of Pharmacy, Cardiff University; Jul. 18, 2016.

Vorburggen, H. et al. "Nucleoside synthesis with trimethyl silyl triflate and perchlorate as catalysts," Chem. Ber. 114, 1234-1255 Berlin 65, 1981.

* cited by examiner

FLOXURIDINE SYNTHESIS

RELATED APPLICATIONS

This application is the U.S. national phase of International Patent Application No. PCT/GB2018/052662, filed Sep. 18, 2018, which claims the benefit of priority of United Kingdom Patent Application No. GB 1715011.1, filed Sep. 18, 2017, the contents of which are hereby incorporated by reference in their entirety.

FIELD OF THE INVENTION

The present invention generally relates to a novel process for the preparation of floxuridine, an anti-cancer drug and a key intermediate in the synthesis of derivatives of floxuridine, such as NUC-3373 (5-fluoro-2'-deoxyuridine-5-O-[1-naphthyl(benzoxy-L-alaninyl)]phosphate), a further anti-cancer drug.

BACKGROUND OF THE INVENTION

Fluorouracil (5-FU) is a widely used anticancer drug, being used to treat colorectal cancer, esophageal cancer, stomach cancer, pancreatic cancer, breast cancer, cervical cancer, actinic keratosis and basal cell carcinoma. Floxuridine (FUDR) is the corresponding deoxyuridine of 5-FU and is itself used to treat colorectal cancer and kidney cancer.

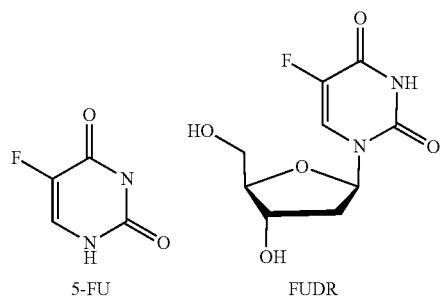

ProTides are masked phosphate derivatives of nucleosides. They have been shown to be particularly potent therapeutic agents in the fields of both antivirals and oncology. ProTides, more specifically, are prodrugs of monophosphorylated nucleosides. These compounds appear to avoid many of the inherent and acquired resistance mechanisms which limit the utility of the parent nucleosides (see, for example, 'Application of ProTide Technology to Gemcitabine: A Successful Approach to Overcome the Key Cancer Resistance Mechanisms Leads to a New Agent (NUC-1031) in Clinical Development', Slusarczyk et al., J. Med. Chem., 2014, 57, 1531-1542).

NUC-3373 (5-fluoro-2'-deoxyuridine-5-O-[1-naphthyl (benzoxy-L-alaninyl)] phosphate) is a ProTide adaptation of FUDR. NUC-3373 and a range of related compounds have shown activity in vitro against a range of cancer models, in many cases, and in particular for NUC-3373, that activity was outstanding and far superior to the results obtained with 5-FU or FUDR. The addition of the ProTide phosphoramidate moiety to the FUDR molecule confers the specific advantages of delivering the key activated form of the agent (FUDR monophosphate) into the tumour cells. Non-clinical studies have demonstrated that NUC-3373 overcomes the key cancer cell resistance mechanisms associated with 5-FU and its oral pro-drug capecitabine, generating high intracellular levels of the active FdUMP metabolite, resulting in a much greater inhibition of tumour cell growth. Furthermore, in formal dog toxicology studies, NUC-3373 is significantly better tolerated than 5-FU (see WO2012/117246; McGuigan et al., 'Phosphoramidate Pro Tides of the anticancer agent FUDR successfully deliver the preformed bioactive monophosphate in cells and confer advantage over the parent nucleoside', J. Med. Chem., 2011, 54, 7247-7258; and Vande Voorde et al., The cytostatic activity of NUC-3073, a phosphoramidate prodrug of 5-fluoro-2'-deoxyuridine, is independent of activation by thymidine kinase and insensitive to degradation by phosphorolytic enzymes'. Biochem. Pharmacol., 2011, 82, 441-452).

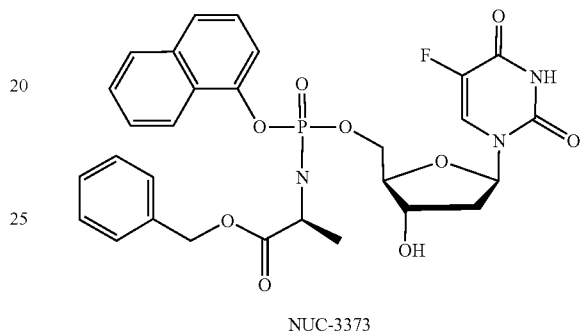

NUC-3373

FUDR is a key intermediate in many synthetic approaches to NUC-3373.

FUDR is typically produced by coupling the sugar portion with the nucleobase. A key factor in the success of this coupling reaction is the diastereoselectivity that is achieved at the anomeric position. In both FUDR and NUC-3373, the 5-FU portion is orientated in the β-position.

A number of prior art routes to FUDR are known. Many of these are several steps long. Aoyama (Bull. Chem. Soc. Jpn., 1987, 60, 2073-2077) has described a shorter route starting from a protected ribofuranosyl chloride and reacting it with 2,4-bis(trimethylsilyloxy)-5-fluoropyrimidine in the presence of nitrophenol in chloroform at 30° C.

It is an aim of certain embodiments of this invention to provide a method of providing FUDR.

It is an aim of certain embodiments of this invention to provide a method of providing the FUDR which is scalable, more economic and/or more efficient than prior art methods. Thus, the method may involve the formation of fewer impurities or lower amounts of particular impurities, particularly the undesired α-anomer of FUDR. The method may provide an increased yield of FUDR.

Certain embodiments of this invention satisfy some or all of the above aims.

SUMMARY OF THE INVENTION

In a first aspect of the invention, is provided a process for the preparation of FUDR in substantially diastereoisomerically pure form:

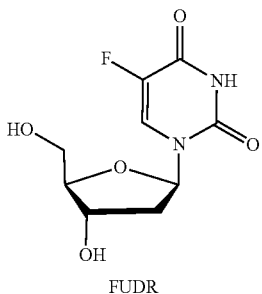

FUDR

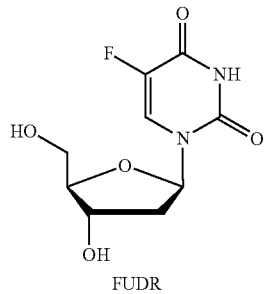

FUDR the process comprising step a) and optionally step b):
 a) reacting a compound of Formula Ia with a compound of Formula IIa in the presence of an acid A1 to provide a compound of Formula IIIa in substantially diastereomerically pure form:

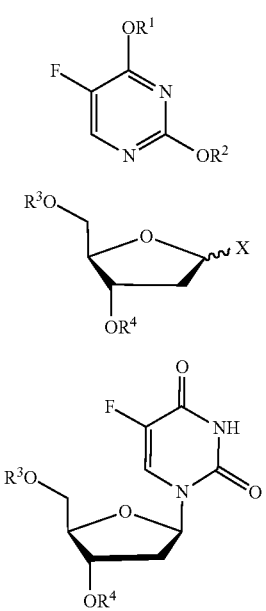

Ia

IIa

IIIa wherein $R^1$ and $R^2$ are each independently trialkylsilyl groups; $R^3$ and $R^4$ are each independently selected from H and a protecting group; and X is a leaving group;
 b) where $R^3$ and/or $R^4$ are protecting groups, optionally removing the protecting group $R^3$ and/or $R^4$ from the compound of formula IIIa to provide FUDR in substantially diastereomerically pure form;
wherein the acid A1 is selected from a Lewis acid, a sulfonic acid, and a carboxylic acid.

The inventors have found that certain acids provide improved reactions relative to those in the prior art, for example the use of certain acids provided higher yields than the acids described in the prior art. In particular, the use of sulfonic acids such as p-toluenesulfonic acid was found to be particularly beneficial.

In the first aspect of the reaction, the step of reacting a compound of Formula Ia with a compound of Formula IIa may be carried out in a solvent S1 selected from acetonitrile (ACN), 1,2-dichloroethane (DCE) and dichloromethane (DCM).

In a second aspect of the invention, is provided a process for the preparation of FUDR in substantially diastereoisomerically pure form:

the process comprising step a) and optionally step b):
 a) reacting a compound of Formula Ia with a compound of Formula IIa in the presence of an acid A1 to provide a compound of Formula IIIa in substantially diastereomerically pure form:

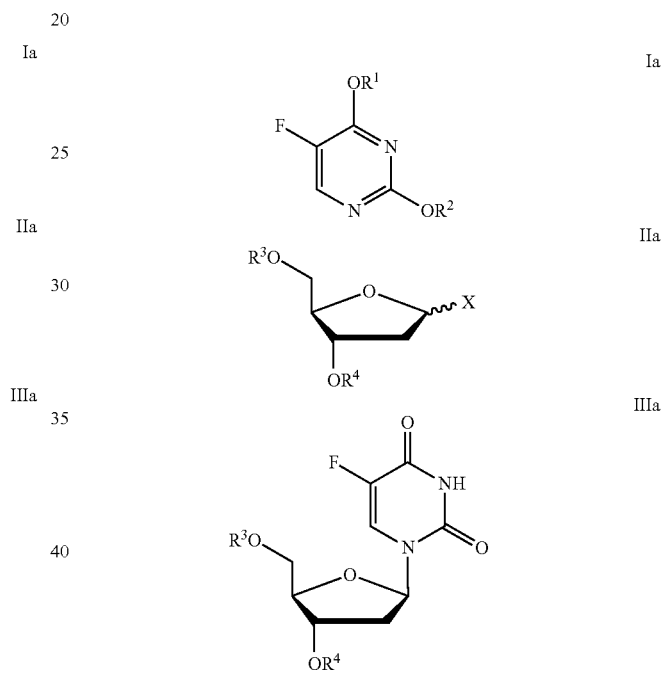

Ia

IIa

IIIa wherein $R^1$ and $R^2$ are each independently trialkylsilyl groups; $R^3$ and $R^4$ are each independently selected from H and a protecting group; and X is a leaving group;
 b) where $R^3$ and/or $R^4$ are protecting groups, optionally removing the protecting group $R^3$ and/or $R^4$ from the compound of formula IIIa to provide FUDR in substantially diastereomerically pure form;
wherein the step of reacting a compound of Formula Ia with a compound of Formula IIa is carried out in a solvent S1 selected from acetonitrile (ACN), 1,2-dichloroethane (DCE) and dichloromethane (DCM).

The inventors have found that carrying out the coupling reaction in certain solvents provides improved reactions relative to those in the prior art including, for example, providing a better selectivity for the desired β-anomer. In particular, the use of DCM was found to be particularly beneficial.

In the first or second aspects of the invention, it may be that the step of reacting a compound of Formula Ia with a compound of Formula IIa is carried out at a temperature T1 that is below room temperature.

In a third aspect of the invention, is provided a process for the preparation of FUDR in substantially diastereoisomerically pure form:

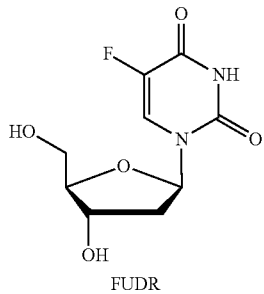

FUDR the process comprising step a) and optionally step b):
a) reacting a compound of Formula Ia with a compound of Formula IIa in the presence of an acid A1 to provide a compound of Formula IIIa in substantially diastereomerically pure form:

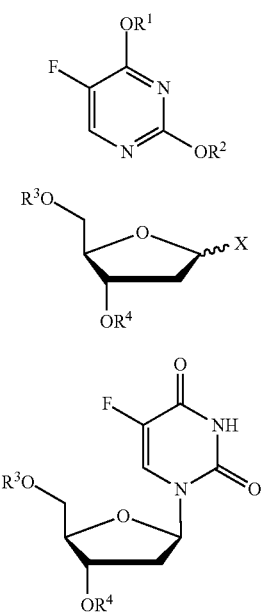

wherein $R^1$ and $R^2$ are each independently trialkylsilyl groups; $R^3$ and $R^4$ are each independently selected from H and a protecting group; and X is a leaving group;
b) where $R^3$ and/or $R^4$ are protecting groups, optionally removing the protecting group $R^3$ and/or $R^4$ from the compound of formula IIIa to provide FUDR in substantially diastereomerically pure form;
wherein the step of reacting a compound of Formula Ia with a compound of Formula IIa is carried out at a temperature T1 below room temperature.

The inventors have found that carrying out the coupling reaction at lower temperatures provides a better selectivity for the desired β-anomer.

In a fourth aspect of the invention, is provided a process for preparing NUC-3373. In this aspect of the invention, a process of the first, second or third aspects of the invention further comprises converting the FUDR to NUC-3373:

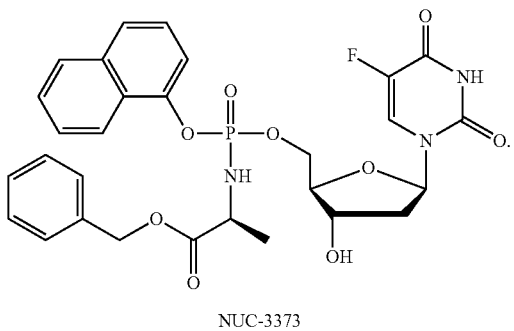

NUC-3373

In a fifth aspect of the invention, is provided FUDR obtainable using the process of any one of the first, second, or third aspects of the invention.

In a sixth aspect of the invention, is provided NUC-3373 obtainable using the process of the fourth aspect of the invention.

The Compound of Formula Ia
Typically, $R^1$ and $R^2$ are the same. It is possible, however, that they may be different.

$R^1$ may be $Si(C_1-C_4-alkyl)_3$. The three $C_1-C_4$-alkyl groups may be the same. $R^1$ may be $Si(C_1-C_3-alkyl)_3$ in which the $C_1-C_3$-alkyl groups are the same. $R^1$ may be $Si(C_1-C_2-alkyl)_3$ in which the $C_1-C_2$-alkyl groups are the same. Exemplary $R^1$ groups include t-butyldimethylsilyl, triisopropylsilyl, triethylsilyl and trimethylsilyl. $R^1$ may be trimethylsilyl.

$R^2$ may be $Si(C_1-C_4-alkyl)_3$. The three $C_1-C_4$-alkyl groups may be the same. $R^2$ may be $Si(C_1-C_3-alkyl)_3$ in which the $C_1-C_3$-alkyl groups are the same. $R^2$ may be $Si(C_1-C_2-alkyl)_3$ in which the $C_1-C_2$-alkyl groups are the same. Exemplary $R^2$ groups include t-butyldimethylsilyl, triisopropylsilyl, triethylsilyl and trimethylsilyl. $R^2$ may be trimethylsilyl.

It may be that $R^1$ and $R^2$ are each trimethylsilyl (TMS). The compound of formula Ia may therefore be a compound of formula Ib:

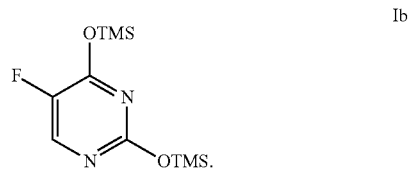

The process may comprise the step of forming the compound of formula Ia. The compound of forming the compound of formula Ia may comprise reacting 5-FU with an appropriate silylating agent SA1, optionally in the presence of a base B1, preferably a nitrogen base. One way of forming compound Ib is described in Aoyama (Bull. Chem. Soc. Jpn., 1987, 60, 2073-2077).

Compound of Formula IIa
Typically, $R^3$ and $R^4$ are the same. It is possible, however, that they may be different.

It may be that $R^3$ is selected from a silyl protecting group, a benzyl protecting group, a carbonate protecting group and an ester protecting group. $R^3$ may be an ester protecting group. $R^3$ may be a benzoyl group. It may be that $R^3$ is a 4-chlorobenzoyl group.

It may be that $R^4$ is selected from a silyl protecting group, a benzyl protecting group, a carbonate protecting group, and an ester protecting group. $R^4$ may be an ester protecting group. $R^4$ may be a benzoyl group. It may be that $R^4$ is a 4-chlorobenzoyl group.

It may be that $R^3$ and $R^4$ are each a benzoyl protecting group. It may be that $R^3$ and $R^4$ are each a 4-chlorobenzoyl group. The compound of formula IIa may be a compound of formula IIb:

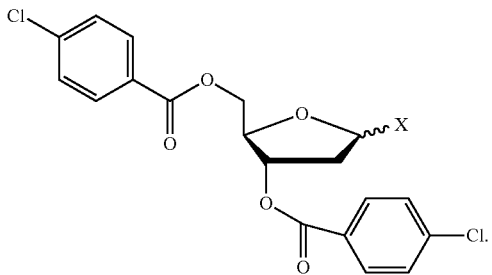

IIb

Where $R^3$ and/or $R^4$ are benzoyl (e.g. 4-chlorobenzoyl), it may be that the step of removing $R^3$ and $R^4$ is carried out using methanolic ammonia solution.

X may be selected from halo, $OC(O)$—$C_1$-$C_4$-alkyl, $O$—$C_1$-$C_4$-alkyl, and OH. X may be selected from halo and $OC(O)$—$C_1$-$C_4$-alkyl. It may be that X is halo. It may be that X is Cl.

The compound of formula IIa may be a compound of formula IIc:

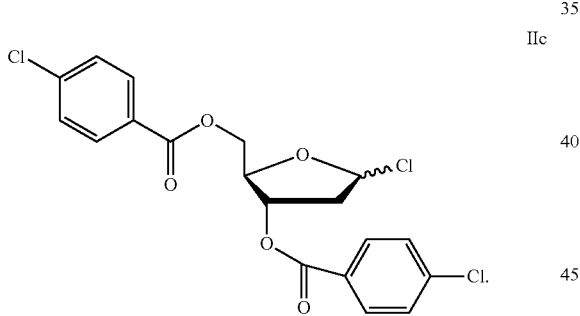

IIc

Reaction Conditions for Coupling Between Compound of Formula Ia and the Compound of Formula IIa A1 may be selected from a Lewis acid, a sulfonic acid, a phenol and a carboxylic acid. A1 may be selected from a Lewis acid, a sulfonic acid, and a carboxylic acid. A1 may be a sulfonic acid. A1 may be selected from camphor sulfonic acid, benzenesulfonic acid, p-toluenesulfonic acid, methanesulfonic acid. The acid may be p-toluenesulfonic acid.

The coupling reaction is carried out in an organic solvent S1. S1 may be selected from a halogenated solvent and acetonitrile. S1 may be selected from dichloromethane, 1,2-dichloroethane and acetonitrile. S1 may be a halogenated solvent. S1 may be selected from dichloromethane and 1,2-dichloroethane. S1 may be dichloromethane.

The coupling reaction is carried out at a temperature T1. T1 may be below room temperature. T1 may be below 25° C. T1 may be below 20° C. T1 may be in the range from 5° C. to 18° C. T1 may be in the range from 9° C. to 15° C.

Converting FUDR to NUC-3373

The process of the first, second or third aspects of the invention may further comprise converting the FUDR to NUC-3373, thus providing a process of providing NUC-3373:

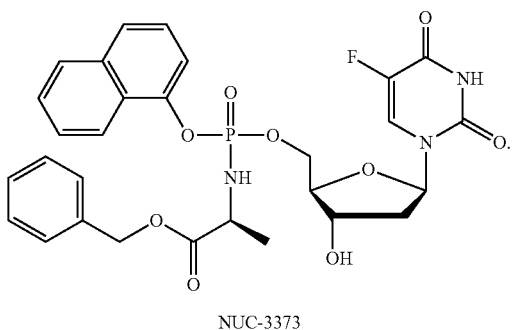

NUC-3373

Thus, the process may comprise step d) and optionally steps c) and e):

c) optionally converting FUDR to a compound of formula Va in which $R^6$ is a protecting group;
d) reacting a compound of Formula IVa; with a compound of Formula Va in presence of a base (B2) to provide a compound of Formula VIa; wherein $R^5$ is a leaving group and $R^6$ is independently selected from H (in which case the compound of formula Va is FUDR) and a protecting group:

Formula IVa

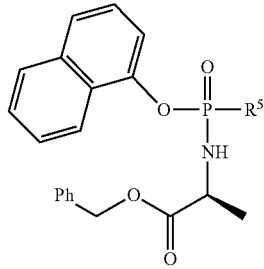

Formula Va

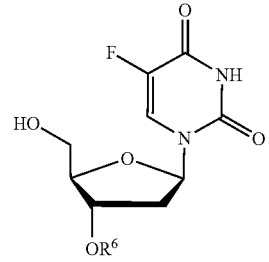

Formula VIa

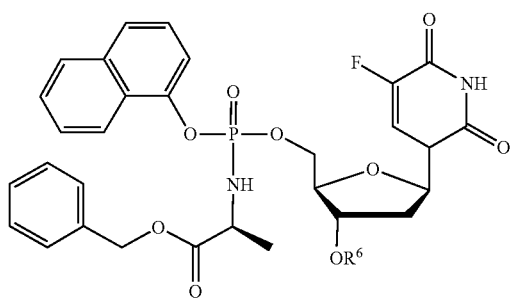

e) where $R^6$ is a protecting group, optionally removing the protecting group $R^6$ from the compound of formula VIa to provide NUC-3373.

An illustrative method for converting FUDR to NUC-3373 is described in WO2012/117246.

$R^6$ may be H.

$R^6$ may be independently selected from silyl protecting group, ester protecting group, carbonate protecting group, benzyl protecting group optionally substituted —C(aryl)$_3$, and —C$_1$-C$_2$-alkyl-O—C$_1$-C$_4$-alkyl.

$R^6$ may be independently selected from optionally substituted —Si(C$_1$-C$_6$-alkyl)$_3$, optionally substituted —C(O)—OC$_1$—C$_6$-alkyl and optionally substituted —C(O)OCH$_2$-aryl, —C(O)—O-allyl. Preferably, $R^6$ is selected from —C(O)OtBu, and —C(O)O-benzyl. Thus, $R^6$ may be —C(O)OCH$_2$-aryl. $R^6$ may be —C(O)OtBu.

Alternatively, $R^6$ may be independently selected from optionally substituted —C(O)—C$_1$-C$_6$-alkyl and optionally substituted —C(O)-aryl, e.g. $R^6$ may be independently selected from benzoyl and acetyl.

In a further alternative, $R^6$ may be optionally substituted —Si(C$_1$-C$_6$-alkyl)$_3$. $R^6$ may be —Si(C$_1$-C$_4$-alkyl)$_3$. The alkyl groups may be unsubstituted. $R^6$ may be t-butyldimethylsilyl.

$R^5$ may be halo. $R^5$ may be a sulfonate. $R^5$ may be a phenolic leaving group in which the phenol is substituted with from 1 to 5 electron withdrawing groups.

NUC-3373 can exist in two diastereomeric forms, differing in the configuration about the phosphorous chiral centre. The diastereoisomer having the (S)-configuration at the phosphorous is known herein as the (Sp)-Nuc-3373 diastereoisomer and the diastereoisomer having the (R)-configuration at the phosphorous chiral centre is known herein as the corresponding (Rp)-diastereoisomer

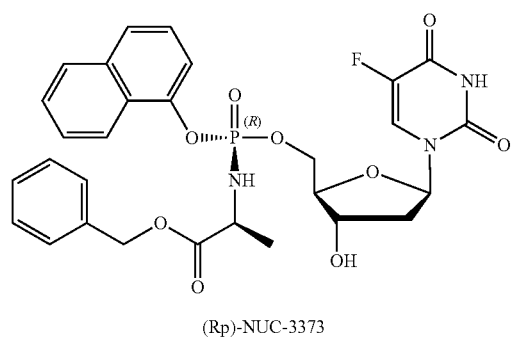

(Rp)-NUC-3373

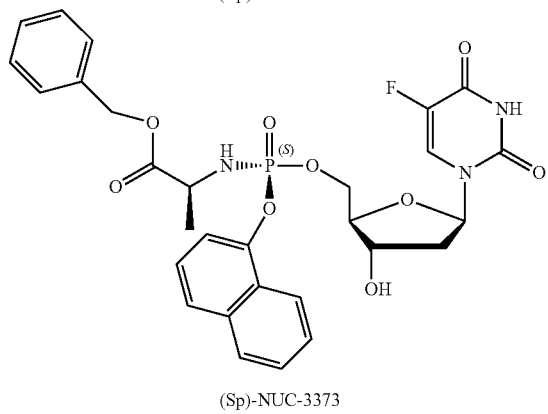

(Sp)-NUC-3373

It may be that the process comprises a method of making NUC-3373 in diastereomerically enriched form with respect to the phosphorous chiral centre. In these embodiments it may be that the compound of formula IVa is a compound of Formula IVb:

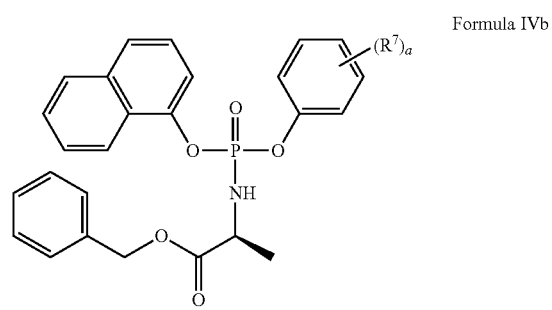

wherein $R^7$ represents an electron withdrawing group and a is an integer from 1 to 5; and wherein the compound of formula IVb is in substantially diastereomerically pure form. Illustrative electron withdrawing groups (e.g. $R^7$ groups) include: halo group (e.g. selected from fluoro, bromo, chloro or iodo); trifluoromethyl, cyano and nitro. a is an integer between 1 and 5. $R^7$ may be at each occurrence halo, e.g. fluoro. For $(R^7)_a$, a may be 5.

As with NUC-3373, compounds of Formula IVb can exist in two diastereomeric forms differing in the configuration about the phosphorous chiral centre (IVc and IVd diastereoisomers). The identity and position of the $R^7$ groups on the phenoxy leaving group may affect the priority (according to the Cahn-Ingold-Prelog rules) of the various groups attached to the phosphorous so the generic formulae IVc and IVd cannot be assigned as Rp or Sp.

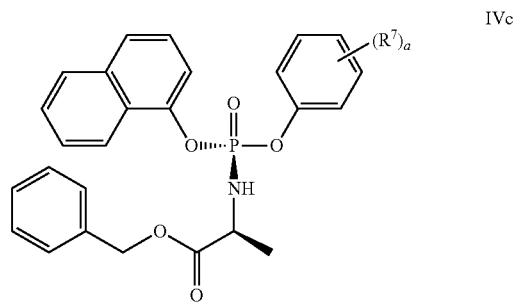

IVc

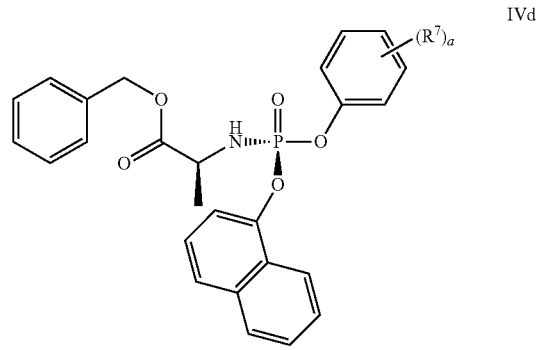

IVd

Displacement of the substituted phenoxy leaving group takes place with inversion of phosphate stereocentre. Thus, the IVc diastereomer provides the (Sp)-diastereoisomer of NUC-3373 and IVd provides the (Rp)-diastereoisomer of NUC-3373.

Thus, it may be that the process comprises converting FUDR into the (Sp)-diastereoisomer of NUC-3373 in diastereomerically enriched form, and the compound of formula IVb is the IVc diastereoisomer in diastereomerically enriched form.

Thus, it may be that the process comprises converting FUDR into the (Rp)-diastereoisomer of NUC-3373 in diastereomerically enriched form, and the compound of formula IVb is the IVd diastereomer in diastereomerically enriched form.

The base (B2) might be a nitrogen base. Alternatively, the base (B2) may be an organometallic base or metal hydride base (e.g. NaH). Thus, the base may be a Grignard reagent (i.e. an alkylmagnesium halide).

Step d) may be carried out in a solvent S2. Where step d) is conducted in the presence of a Grignard reagent, the organic solvent S2 is preferably an ether. Most preferably, the solvent S2 is tetrahydrofuran.

The process may comprise the diastereoisomeric enrichment of a compound of Formula IVb; the process comprising:
x) suspending or dissolving the IVd diastereoisomer of a compound of Formula IVb; or a mixture of the IVc and IVd diastereoisomers of a compound of Formula IVb in a solvent (S3),
y) treating the solution or suspension with a base (B3) to obtain the IVc diastereoisomer in substantially diastereomerically enriched form, and
z) isolating the IVc diastereoisomer of a compound of formula IVb.

The IVc diastereoisomer of a compound of formula IVb can then be used in step d) of the process described above to provide (Sp)-NUC-3373.

The inventors have surprisingly found that upon treating compounds of formula IVb with a base, they isomerise, preferentially forming the IVc diastereoisomer over the IVd diastereoisomer. Thus, the IVd diastereoisomer can be converted to the IVc diastereoisomer or an epimeric mixture of the IVd diastereoisomer and the IVc diastereoisomer can be converted to the IVc diastereoisomer. This increases the net efficiency of any synthetic sequence for making the (Sp)-diastereoisomer of NUC-3373.

The base (B3) may be selected from the group consisting of organic amine bases (e.g. primary, secondary, tertiary amines, cyclic amine; exemplary organic amine bases include bases include N-alkylimidazoles, (e.g. N-methyl imidazole (NMI)), imidazole, optionally substituted pyridines, (e.g. collidine, pyridine, 2,6-lutidine) and trialkylamines (e.g. triethylamine, and diisopropylethylamine)); or inorganic bases (e.g. alkali metal hydroxide, alkali metal carbonates, alkali metal alkoxides, alkali metal aryloxides). Preferably, B3 is a tertiary amine. Thus, B3 may be a trialkylamine. Most preferably, B3 is triethylamine.

The solvent S3 may be selected from the group consisting of amides, ethers, esters, ketones, aromatic hydrocarbons, halogenated solvents, nitriles, sulfoxides, sulfones and mixtures thereof. S3 may be an organic solvent. Organic solvents include but are not limited to ethers (e.g. tetrahydrofuran, 1,4-dioxane, diethyl ether, t-butylmethylether); ketones (e.g. acetone and methyl isobutyl ketone); halogenated solvents (e.g. dichloromethane, chloroform and 1,2-dichloroethane); hydrocarbons (e.g. cyclohexane, pentane, hexane, heptane), aromatic solvents (e.g. benzene and toluene), esters (e.g. ethyl acetate) and amides (e.g. DMF, NMP); or mixtures thereof. Preferably, S3 is a hydrocarbon or is a mixture comprising a hydrocarbon. Where S3 is a mixture, it may be a mixture that comprises over 50% (e.g. over 70%) of the hydrocarbon S3 may be a hydrocarbon. The hydrocarbon may be hexane. The hydrocarbon may be heptane. S3 may be a mixture of hexane or heptane and a relatively more polar organic solvent (e.g. an ether, ester, alcohol or halogenated solvent). S3 may be a mixture of hexane or heptane and a polar organic solvent, the mixture comprising over 50% (e.g. over 70%) by volume hexane or heptane. S3 may be a mixture of hexane or heptane and ethyl acetate. S3 may be a mixture of heptane and ethyl acetate. S3 may be a mixture of hexane or heptane and ethyl acetate, the mixture that comprising over 50% (e.g. over 70%) by volume hexane or heptane. S3 may be a mixture of heptane and ethyl acetate, the mixture comprising over 50% (e.g. over 70%) by volume heptane. S3 may be a mixture of hexane or heptane and methyl-tert-butyl ether. S3 may be a mixture of hexane and methyl-tert-butyl ether. S3 may be a mixture of hexane or heptane and methyl-tert-butyl ether, the mixture that comprising over 50% (e.g. over 70%) by volume hexane or heptane. S3 may be a mixture of hexane and methyl-tert-butyl ether, the mixture comprising over 50% (e.g. over 70%) by volume hexane.

Step y) may involve stirring the mixture of the compound of formula IVb and the base B3 for 24 h or longer. Step y) may involve stirring the mixture of the compound of formula IVb and the base B3 for 48 h or longer. Step y) may involve stirring the mixture of the compound of formula IVb and the base B3 for 60 h or longer. Step y) may involve stirring the mixture of the compound of formula IVb and the base B3 for 72 h or longer. Step y) may involve stirring the mixture of the compound of formula IVb and the base B3 for up to 100 h.

In certain specific embodiments, the compound of Formula IVb is a compound selected from:

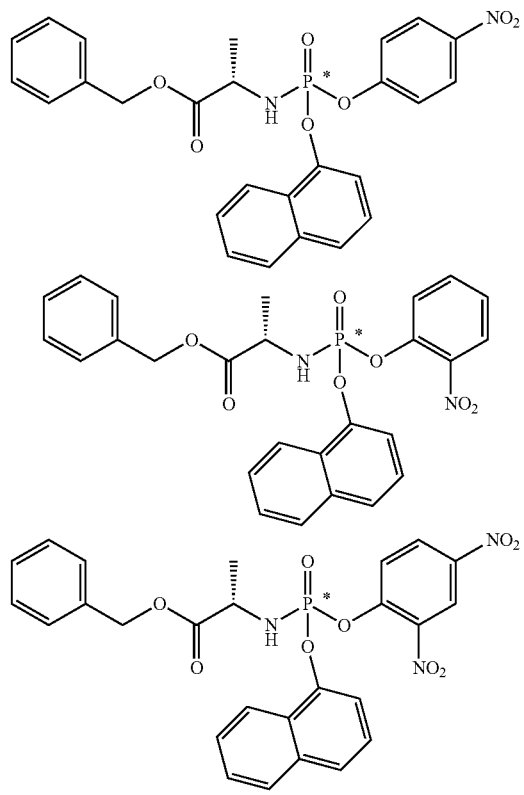

-continued
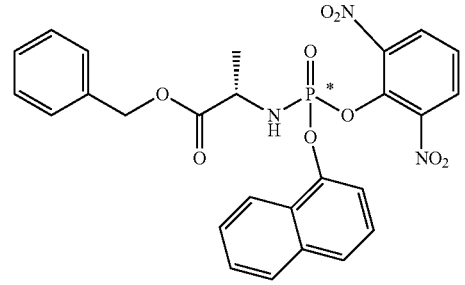
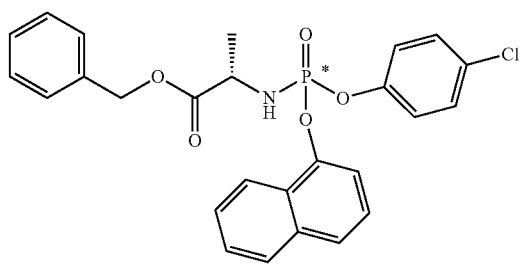
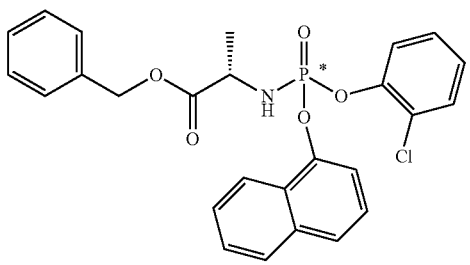
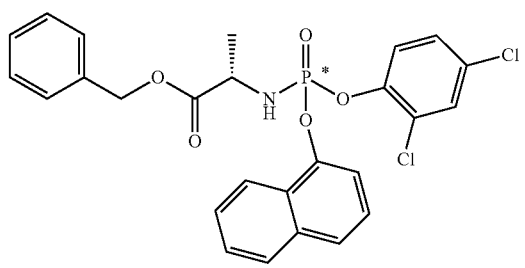
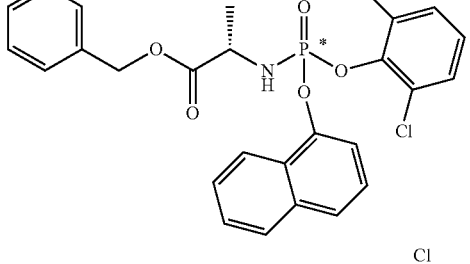
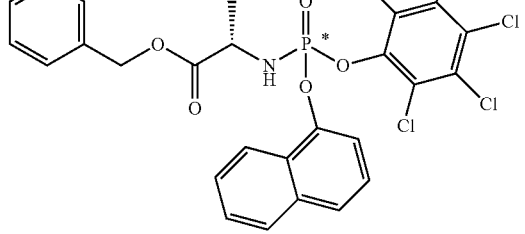
-continued
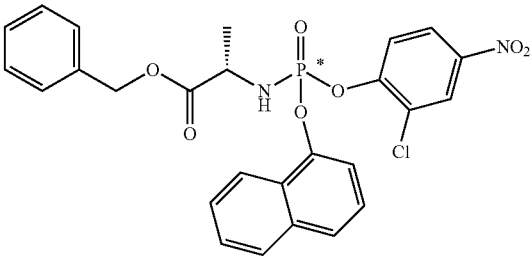
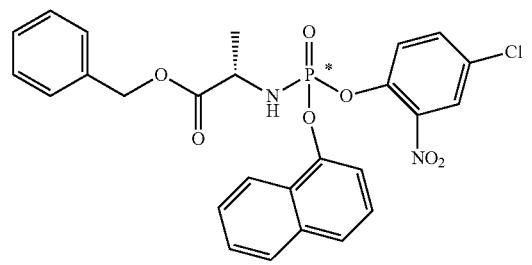
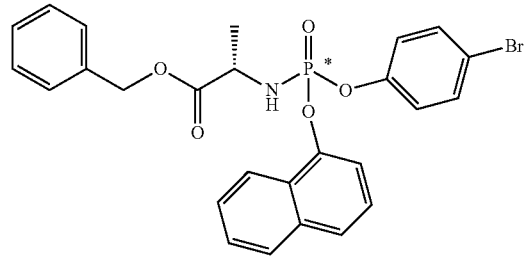
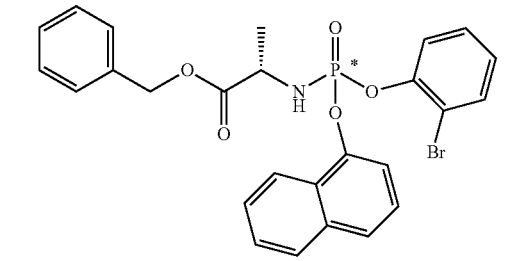
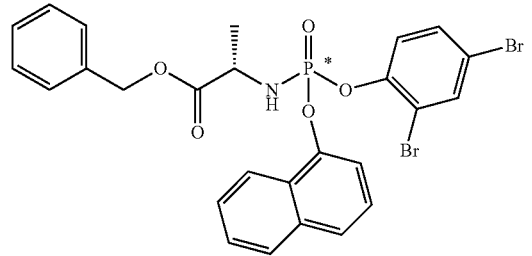
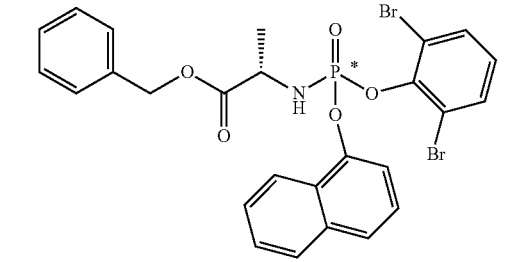

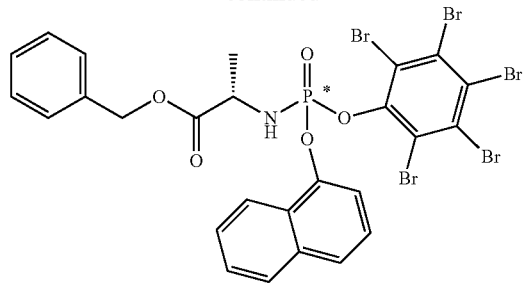
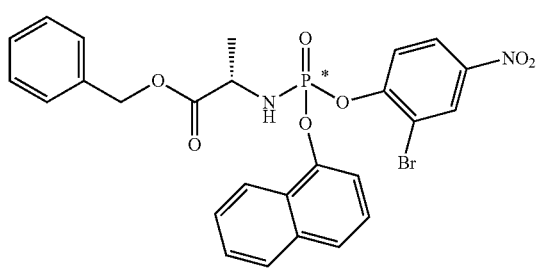
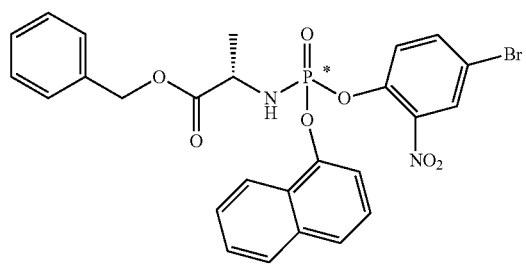
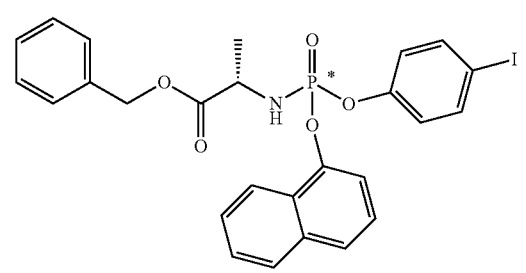
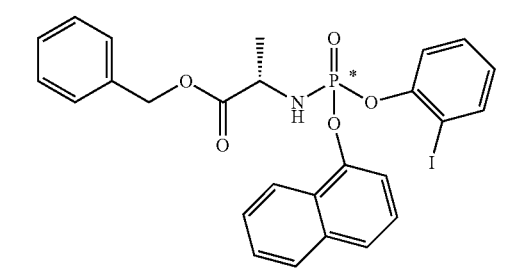
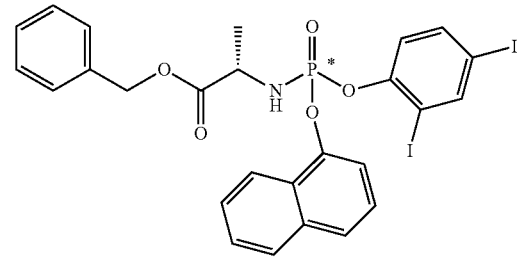
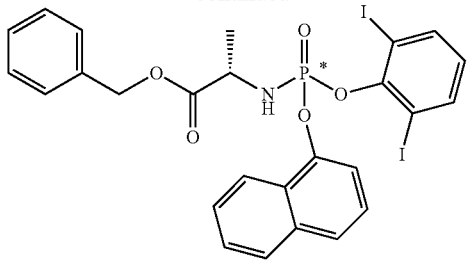
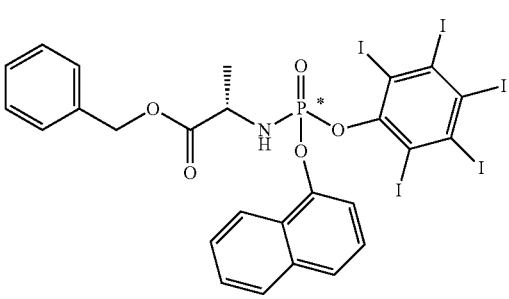
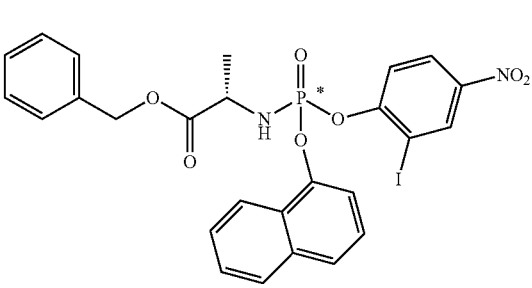
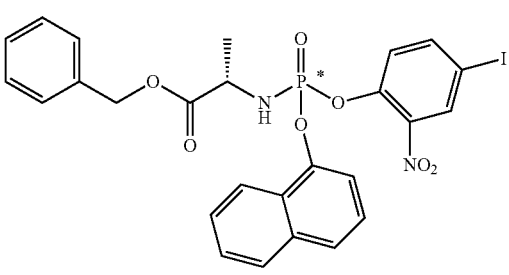
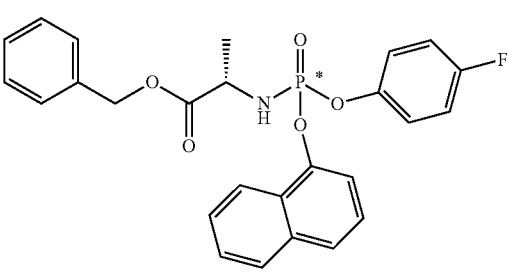
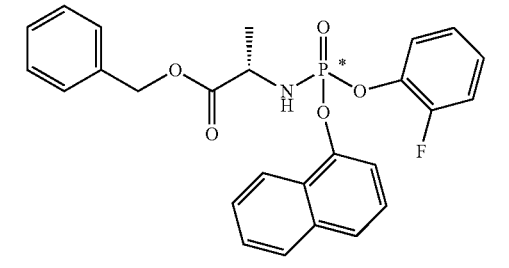

-continued
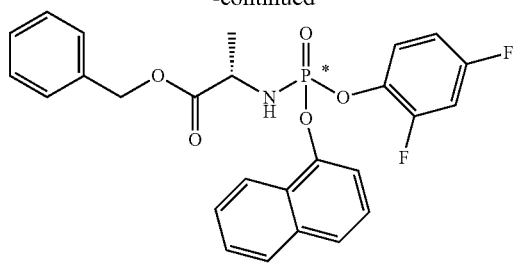
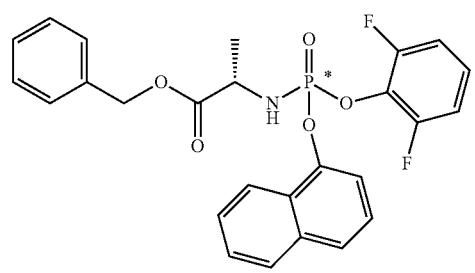
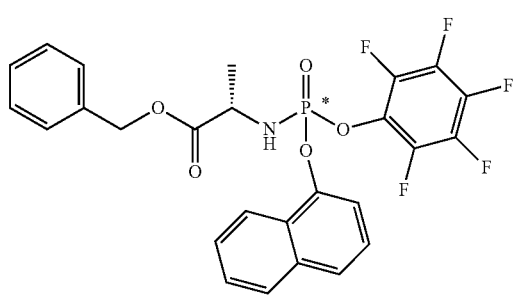
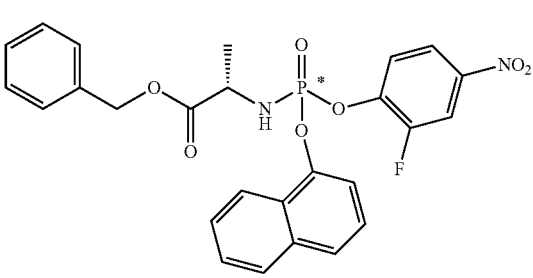
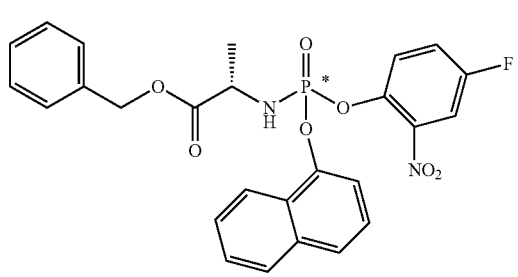
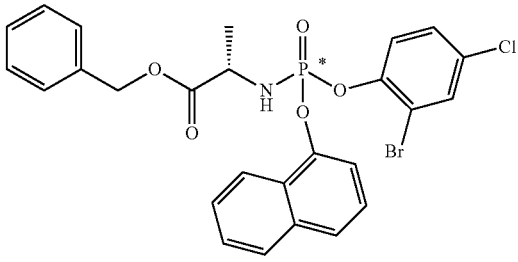
-continued
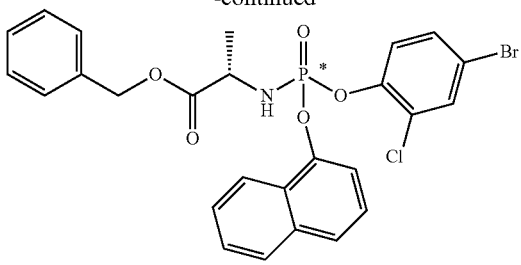
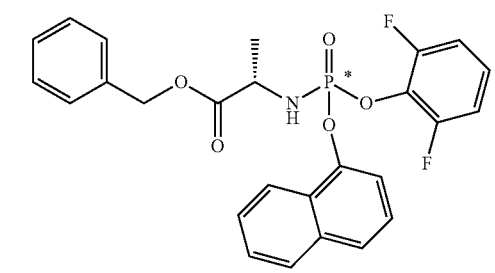
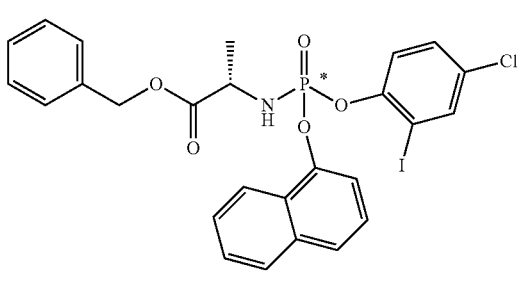
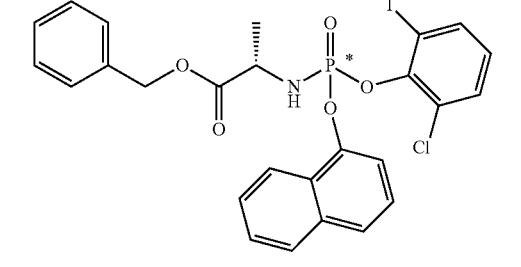
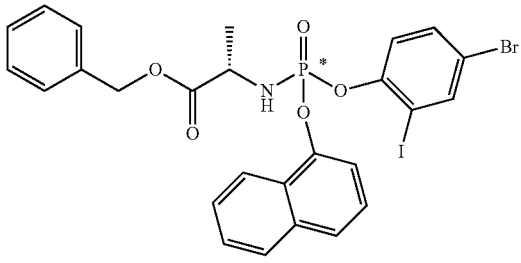
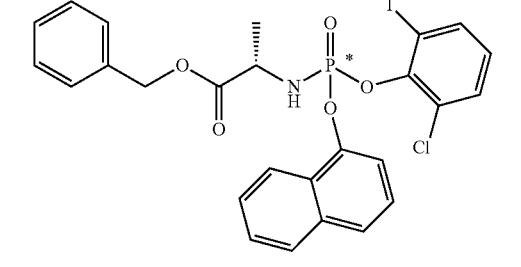

19
-continued
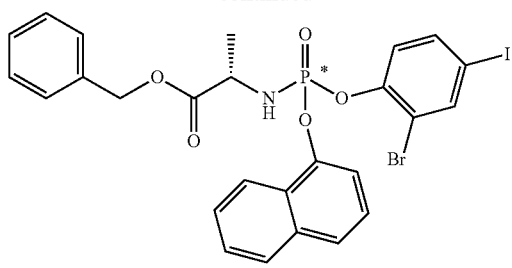
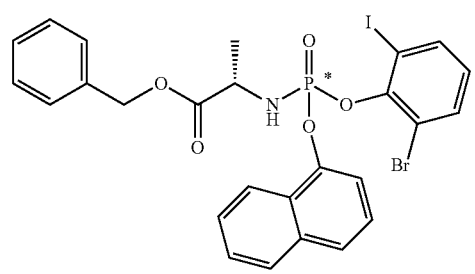
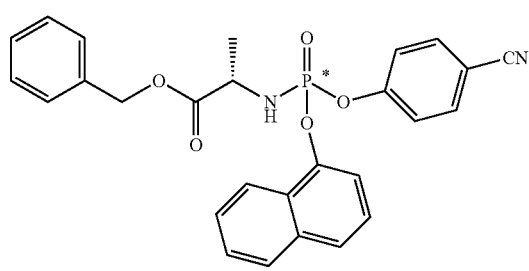
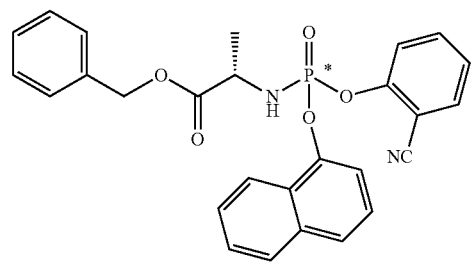
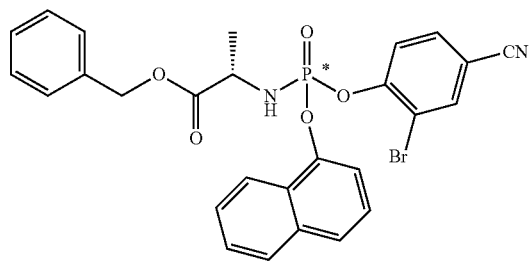
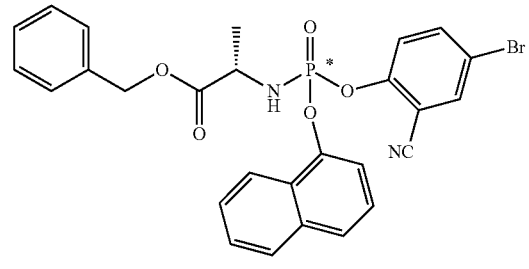
20
-continued
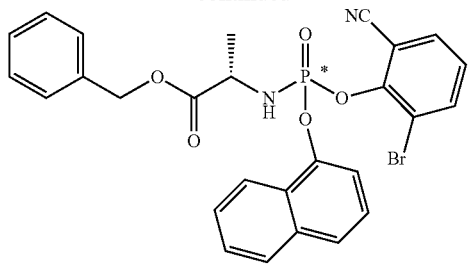
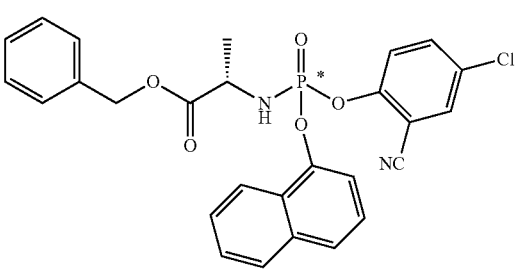
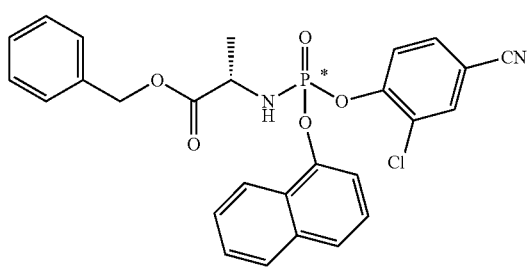
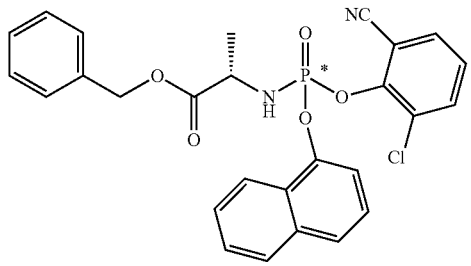
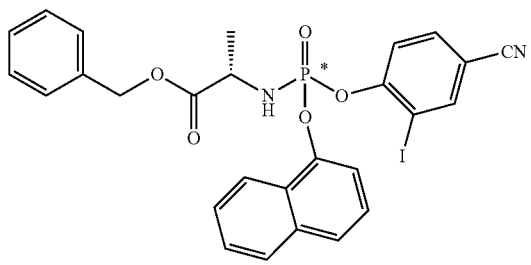
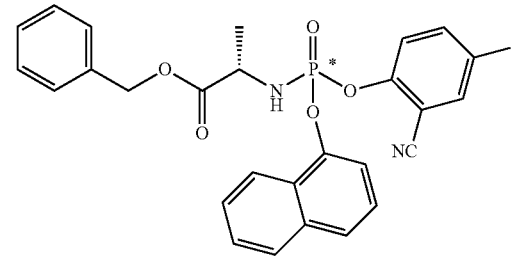

21
-continued
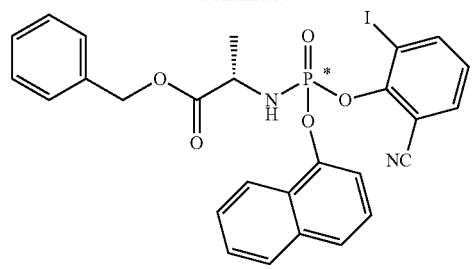
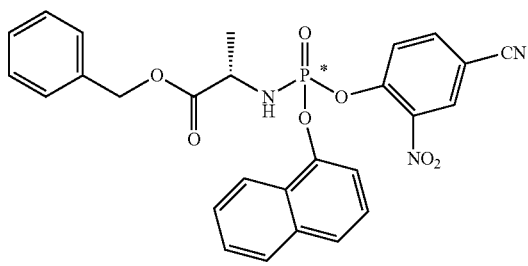
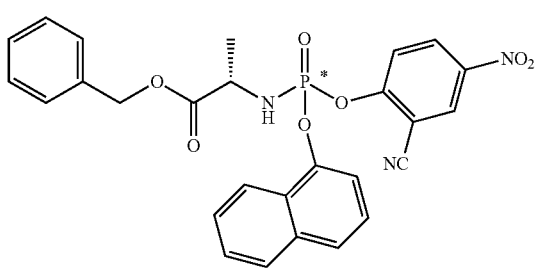
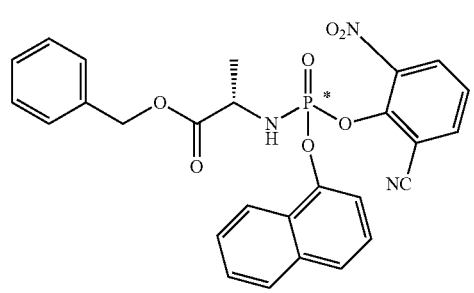
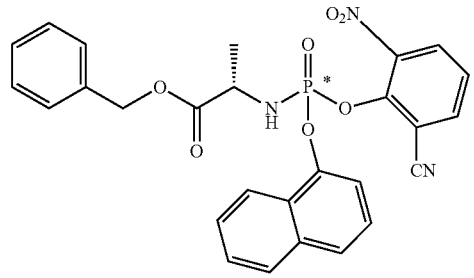
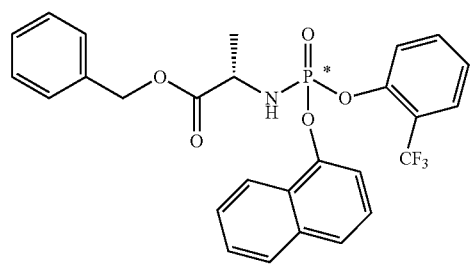
22
-continued
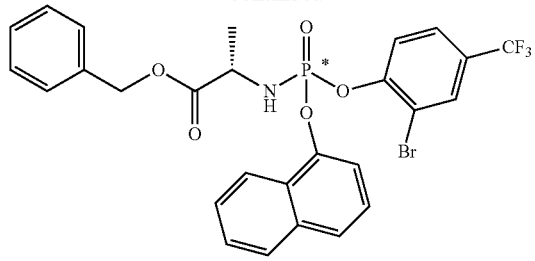
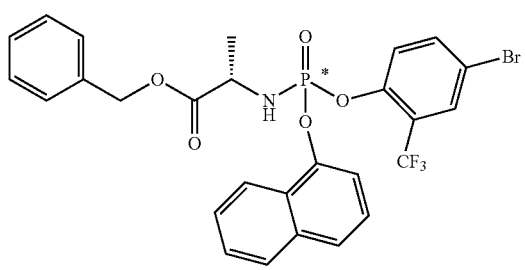
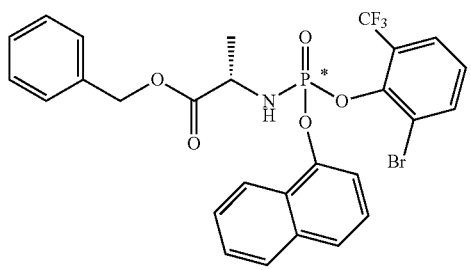
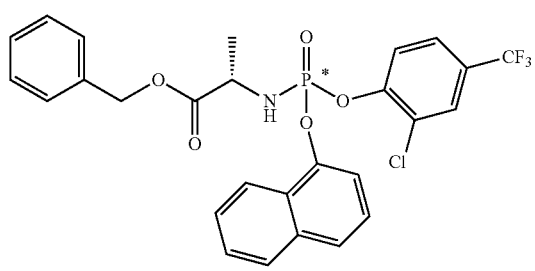
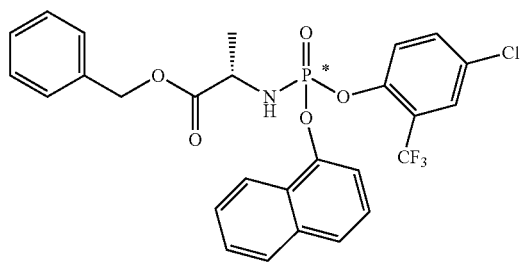
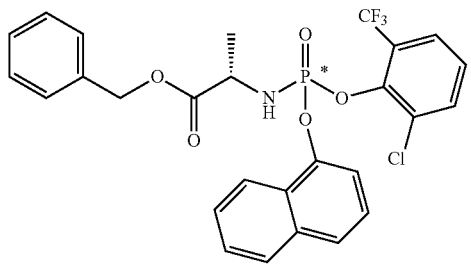

-continued

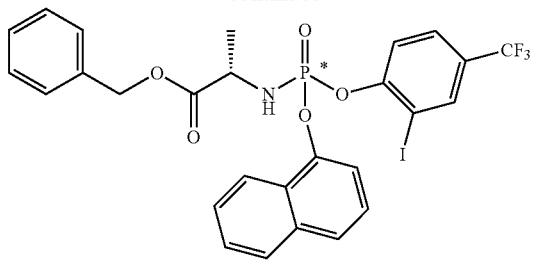
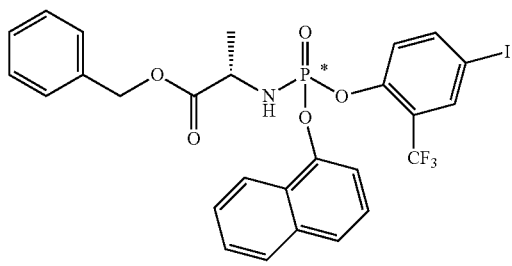
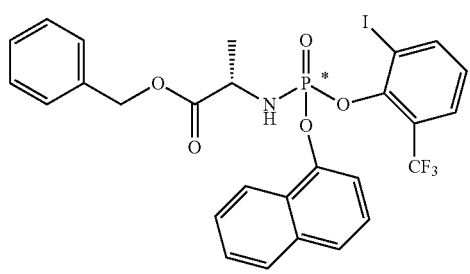
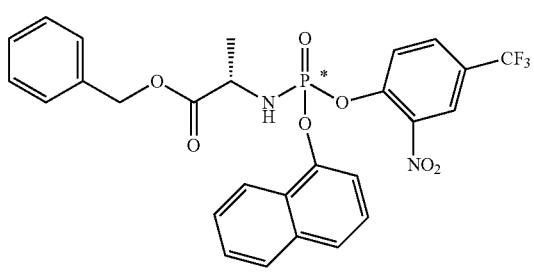
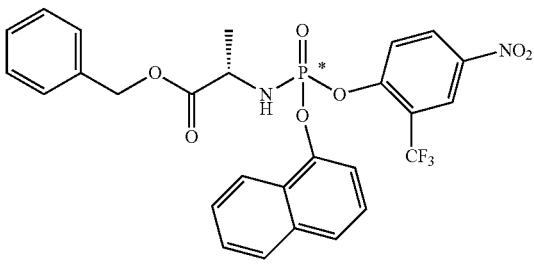
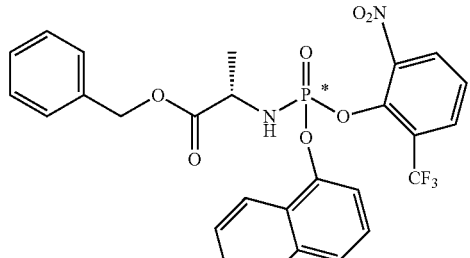

The compound of formula IVb may be compound IVe:

compound IVe

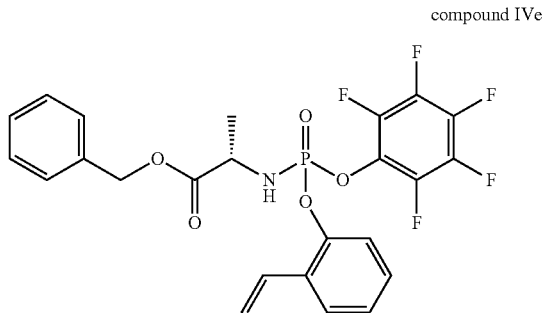

The compound of formula IVb may be compound IVf:

compound IVf

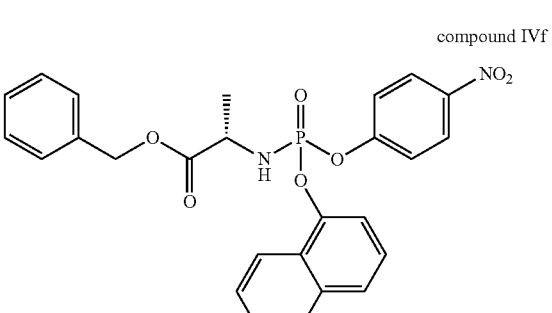

Formulations and Uses of the Products of the Methods of the Invention

The invention may also provide a pharmaceutical composition comprising a compound of the fifth and sixth aspects of the invention and a pharmaceutically acceptable excipient.

The invention may also provide a method of treating cancer (e.g. a solid tumour or leukaemia), the method comprising administering to a subject in need thereof a therapeutically effective amount of a compound of the fifth and sixth aspects of the invention.

The compounds of the fifth and sixth aspects of the invention may be for medical use. The compounds of the fifth and sixth aspects of the invention may be for use in treating cancer (e.g. a solid tumour or leukaemia).

The present application and invention further include the subject matter of the following numbered clauses:

1. A process for the preparation of FUDR in substantially diastereoisomerically pure form:

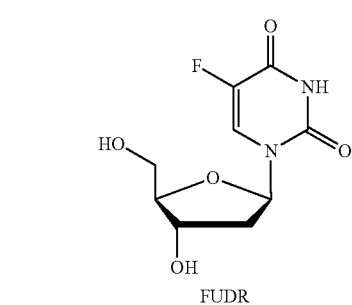

FUDR the process comprising step a) and optionally step b):
a) reacting a compound of Formula Ia with a compound of Formula IIa in the presence of an acid A1 to provide a compound of Formula IIIa in substantially diastereomerically pure form:

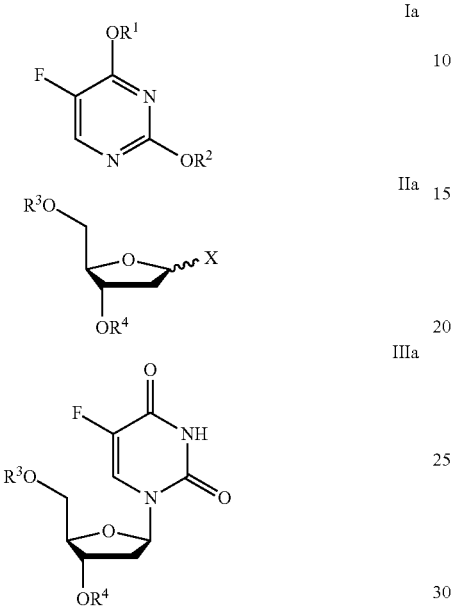

wherein $R^1$ and $R^2$ are each independently trialkylsilyl groups; $R^3$ and $R^4$ are each independently selected from H and a protecting group; and X is a leaving group;
b) where $R^3$ and/or $R^4$ are protecting groups, optionally removing the protecting group $R^3$ and/or $R^4$ from the compound of formula IIIa to provide FUDR in substantially diastereomerically pure form;

wherein the acid A1 is selected from a Lewis acid, a sulfonic acid and a carboxylic acid.

2. A process of clause 1, wherein the step of reacting a compound of Formula Ia with a compound of Formula IIa is carried out in a solvent S1 selected from acetonitrile (ACN), 1,2-dichloroethane (DCE) and dichloromethane (DCM).

3. A process for the preparation of FUDR in substantially diastereoisomerically pure form:

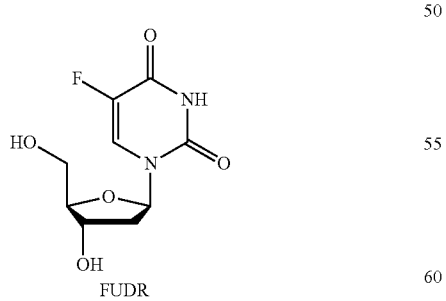
FUDR the process comprising step a) and optionally step b):
a) reacting a compound of Formula Ia with a compound of Formula IIa in the presence of an acid A1 to provide a compound of Formula IIIa in substantially diastereomerically pure form:

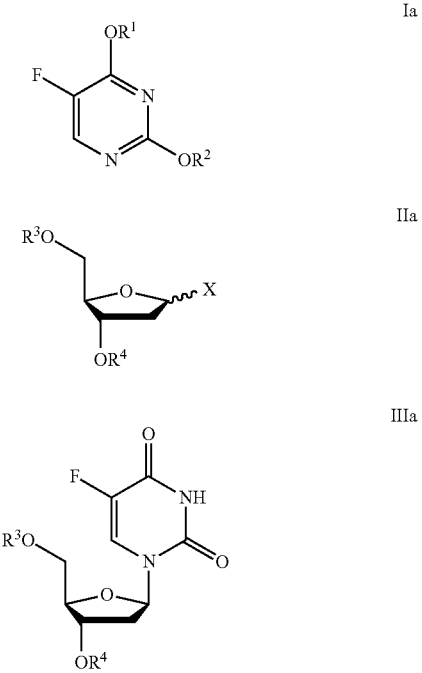

wherein $R^1$ and $R^2$ are each independently trialkylsilyl groups; $R^3$ and $R^4$ are each independently selected from H and a protecting group; and X is a leaving group;
b) where $R^3$ and/or $R^4$ are protecting groups, optionally removing the protecting group $R^3$ and/or $R^4$ from the compound of formula IIIa to provide FUDR in substantially diastereomerically pure form;

wherein the step of reacting a compound of Formula Ia with a compound of Formula IIa is carried out in a solvent S1 selected from acetonitrile (ACN), 1,2-dichloroethane (DCE) and dichloromethane (DCM).

4. A process of any preceding clause, wherein the step of reacting a compound of Formula Ia with a compound of Formula IIa is carried out at a temperature T1 that is below room temperature.

5. A process for the preparation of FUDR in substantially diastereoisomerically pure form:

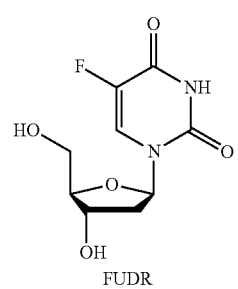
FUDR the process comprising step a) and optionally step b):
a) reacting a compound of Formula Ia with a compound of Formula IIa in the presence of an acid A1 to provide a compound of Formula IIIa in substantially diastereomerically pure form:

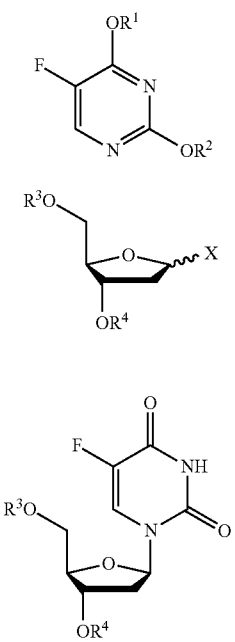

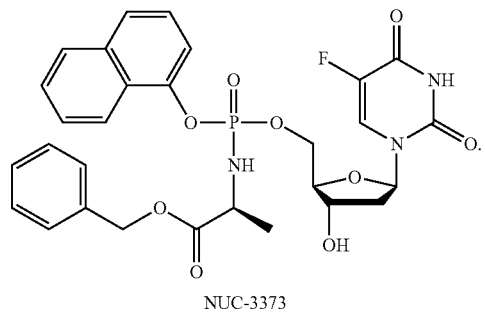

NUC-3373 wherein $R^1$ and $R^2$ are each independently trialkylsilyl groups; $R^3$ and $R^4$ are each independently selected from H and a protecting group; and X is a leaving group;

b) where $R^3$ and/or $R^4$ are protecting groups, optionally removing the protecting group $R^3$ and/or $R^4$ from the compound of formula IIIa to provide FUDR in substantially diastereomerically pure form;

wherein the step of reacting a compound of Formula Ia with a compound of Formula IIa is carried out at a temperature T1 below room temperature.

6. A process of any preceding clause, wherein the acid is a sulfonic acid.

7. A process of clause 6, wherein the acid is p-toluenesulfonic acid.

8. A process of any preceding clause, wherein the step of reacting a compound of Formula Ia with a compound of Formula IIa is carried out in a solvent S1 that is dichloromethane (DCM).

9. A process of any preceding clause, wherein the step of reacting a compound of Formula Ia with a compound of Formula IIa is carried out at a temperature T1 that is below 20° C.

10. A process of claim 9, wherein T1 is in the range from 9° C. to 15° C.

11. A process of any preceding clause, wherein $R^1$ and $R^2$ are each trimethylsilyl.

12. A process of any preceding clause, wherein $R^3$ and $R^4$ are each a 4-chlorobenzoyl group.

13. A process of clause 7, wherein $R^3$ and $R^4$ are removed using methanolic ammonia solution.

14. A process of any preceding clause, wherein X is Cl.

15. A process of any preceding clause, wherein the process further comprises converting the FUDR to NUC-3373:

16. A process of clause 15, wherein the FUDR is converted to NUC-3373 in a process comprising step d) and optionally comprising steps c) and e):

c) optionally converting FUDR to a compound of formula Va in which $R^6$ is a protecting group;

d) reacting a compound of Formula IVa; with a compound of Formula Va in presence of a base (B2) to provide a compound of Formula VIa; wherein $R^5$ is a leaving group and $R^6$ is independently selected from H (in which case the compound of formula Va is FUDR) and a protecting group:

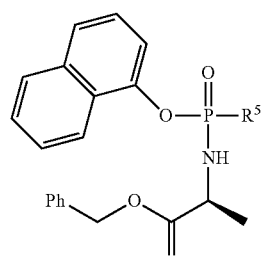

Formula IVa

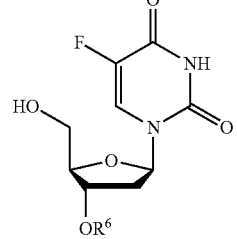

Formula Va

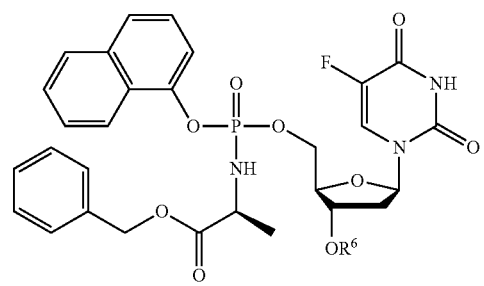

Formula VIa e) where $R^6$ is a protecting group, optionally removing the protecting group $R^6$ from the compound of formula VIa to provide NUC-3373.

17. FUDR obtainable using the process of any one of clauses 1 to 14.

18. NUC-3373 obtainable using the process of clause 15 or clause 16.

DETAILED DESCRIPTION

A protecting group for a hydroxyl group (e.g. $R^3$, $R^4$ or $R^6$) may be independently selected from silyl protecting group, ester protecting group, carbonate protecting group, benzyl protecting group optionally substituted —C(aryl)$_3$, and —C$_1$-C$_2$-alkyl-O—C$_1$-C$_4$-alkyl.

Methods of accessing the protected compounds of Formula IIa, IIb or Va are known in the art and/or can be prepared by known methods. For example compounds of Formula Va may be synthesized from FUDR by protecting the hydroxy groups with suitable protecting groups. The protecting groups can typically be added and removed using conventional protecting group methodology, for example, as described in "Protective Groups in Organic Chemistry," edited by J W F McOmie (1973); "Greene's Protective Groups in Organic Synthesis," 5$^{th}$ edition, G. M. Wuts (2014); and "Protecting Groups", 3$^{rd}$ eddition P. J Kocienski (1995).

It will typically be necessary to prepare the compounds of formula Va by first protecting the 5'-hydroxy group of FUDR with a protecting group which is orthogonal to those which will be used to protect the 3' hydroxy (i.e. a group which can be removed from the 5'-hydroxyl group without also removing the desired 3'-hydroxyl, protecting group). Simultaneously or subsequently, the 3'-hydroxyl groups are protected with the desired protecting group(s) and the 5'-hydroxyl protecting group can be removed to generate the compound of formula Va, Certain protecting groups can be simultaneously introduced onto the 3'-hydroxyl and 5'-hydroxyl and then selectively removed from the 5' hydroxyl group without being removed from the 3' hydroxyl group.

Alternatively, it may be that $R^3$ and $R^6$ are the same protecting group and that $R^4$ is a protecting group that is orthogonal to that group (i.e. $R^4$ is a group which can be removed from the 5'-hydroxyl group without also removing the $R^3/R^6$ protecting group). In this instance, step b) comprises removing the protecting group from $R^4$ to provide a compound of formula Va but leaving $R^3$. The compound of formula Va can then be subjected to steps d) and e).

A silyl protecting group is typically an optionally substituted —Si(C$_1$-C$_6$-alkyl)$_3$ group. A silyl protecting group can also be a t-butyldimethylsilyl group. The group optionally substituted —Si(C$_1$-C$_6$-alkyl)$_3$ may be a —Si(C$_1$-C$_4$-alkyl)$_3$ group. The group is (i.e. the alkyl groups are) preferably unsubstituted. Illustrative examples include triethylsilyl, triisopropylsilyl and t-butyldimethylsilyl.

An ester protecting group may be selected from optionally substituted —C(O)—C$_1$-C$_6$-alkyl and optionally substituted —C(O)-aryl.

The group optionally substituted —C(O)—C$_1$-C$_6$-alkyl may be a —C(O)—C$_1$-C$_6$-alkyl group. The group (i.e. the alkyl group) is preferably unsubstituted. Illustrative examples include acetyl and propionyl.

The group optionally substituted —C(O)-aryl may be a —C(O)-phenyl group. —C(O)-phenyl groups may also be known as benzoyl protecting groups. The group (i.e. the phenyl group) may be substituted or unsubstituted. Illustrative examples include benzoyl and 4-chlorobenzoyl.

A carbonate protecting group may be selected from optionally substituted —C(O)—C$_1$-C$_6$-alkyl, optionally substituted —C(O)OCH$_2$-aryl, —C(O)—O-allyl and —C(O)—O—CH$_2$-fluorenyl.

The group optionally substituted —C(O)—OC$_1$—C$_6$-alkyl may be a —C(O)—OC$_1$—C$_4$-alkyl group. The group (i.e. the alkyl group) is preferably unsubstituted. Illustrative examples include —C(O)—O-methyl and —C(O)—O-ethyl. A particularly preferred example is C(O)OtBu. The group optionally substituted —C(O)OCH$_2$-aryl is preferably an optionally substituted —C(O)Obenzyl group. Illustrative examples include —C(O)Obenzyl and —C(O)O-(4-methoxybenzyl).

A benzyl protecting group is an optionally substituted —(C$_1$-alkylene)-aryl group. The group optionally substituted —(C$_1$-alkylene)-aryl. Illustrative examples include benzyl, 1-ethylbenzene (—CH(Me)Ph), 4-methoxy benzyl, 4-nitrobenzyl, 4-bromobenzyl, 2,3-dimethoxybenzyl and 2,4-dimethoxybenzyl.

The group optionally substituted —C$_1$-C$_2$-alkyl-O—C$_1$-C$_4$-alkyl may be a —C$_1$-C$_2$-alkyl-O—C$_1$-C$_2$-alkyl group. The group is (i.e. the alkyl groups are) preferably unsubstituted. Illustrative examples include methoxymethyl (MOM) and 2-methoxyethoxymethyl (MEM).

The group optionally substituted —C(aryl)$_3$ may be a —C(phenyl)$_3$ group. Illustrative examples include trityl.

Exemplary Grignard reagents include t-butylmagnesium halides such as t-BuMgCl, t-BuMgBr. Preferably, the base B1 is t-BuMgCl.

Exemplary nitrogen bases include N-alkylimidazoles, (e.g. N-methyl imidazole (NMI)), imidazole, optionally substituted pyridines, (e.g. collidine, pyridine, 2,6-lutidine) and trialkylamines (e.g. triethylamine, and diisopropylethylamine).

Exemplary silylating agents (SA1) include silyl chlorides, silylsulfonates (e.g. triflates) and hexamethyldisilazane.

Exemplary Lewis acids include SnCl$_4$, TiCl$_4$, Ti(OR)$_4$ AlMe$_3$, AlMe$_2$Cl, AlMeCl$_2$, AlCl$_3$, BF$_3$ sources (eg. BF$_3$.OEt$_2$ and BF$_3$.SMe$_2$), BCl$_3$, B(C$_6$F$_5$)$_3$, FeCl$_3$, Yb (OTf)$_3$, InBr$_3$, and thioureas.

Exemplary phenols that can be used as acids in the methods of certain aspects of the invention include those having electron withdrawing groups attached to the benzene ring. Examples include pentafluorophenol, 2-nitrophenol, 3-nitrophenol and 4-nitrophenol.

Exemplary carboxylic acids include alkyl carboxylic acids, e.g. acetic acid, propionic acid and aryl carboxylic acids, e.g. benzoic acid.

Exemplary sulfonic acids include camphor sulfonic acid, benzenesulfonic acid, p-toluenesulfonic acid, methanesulfonic acid.

Throughout this specification, 'diastereomerically enriched form' and 'substantially diastereomerically pure form' means a diastereoisomeric purity of greater than 95%. 'Diastereomerically enriched form' and 'substantially diastereomerically pure form' may mean a diastereoisomeric purity of greater than 98%, greater than 99% or greater than 99.5%.

Any of the aforementioned alkyl and aryl (e.g. phenyl, including the phenyl groups in benzyl groups) groups, are optionally substituted, where chemically possible, by 1 to 3 substituents which are each independently at each occurrence selected from the group consisting of: oxo, =NR$^a$, =NOR$^a$, halo, nitro, cyano, NR$^a$R$^a$, NR$^a$S(O)$_2$R$^a$, NR$^a$-CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$C(O)R$^a$, CONR$^a$R$^a$, C$_1$-C$_4$-alkyl, C$_2$-C$_4$-alkenyl, and C$_1$-C$_4$ haloalkyl; wherein R$^a$ is independently at each occurrence selected from H, C$_1$-C$_4$ alkyl and C$_1$-C$_4$ haloalkyl.

It may be that any of the aforementioned alkyl groups are unsubstituted.

It may be that any of the aforementioned aryl groups (e.g. phenyl, including the phenyl groups in benzyl groups) are optionally substituted, where chemically possible, by 1 to 3 substituents which are each independently at each occurrence selected from the group consisting of: halo, nitro, cyano, $NR^aR^a$, $NR^aS(O)_2R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^aC(O)R^a$, $CONR^aR^a$, $C_1$-$C_4$-alkyl, $C_2$-$C_4$-alkenyl, $C_2$-$C_4$-alkenyl, and $C_1$-$C_4$ haloalkyl; wherein $R^a$ is independently at each occurrence selected from H, $C_1$-$C_4$ alkyl and $C_1$-$C_4$ haloalkyl.

It may be that any of the aforementioned aryl (e.g. phenyl, including the phenyl groups in benzyl groups) groups are optionally substituted by 1 to 3 substituents which are each independently at each occurrence selected from the group consisting of: halo, nitro, $OR^a$; $C_1$-$C_4$-alkyl, $C_1$-$C_4$ haloalkyl; wherein $R^a$ is independently at each occurrence selected from H, $C_1$-$C_4$ alkyl and $C_1$-$C_4$ haloalkyl.

Aryl groups have from 6 to 20 carbon atoms as appropriate to satisfy valency requirements. Aryl groups are carbocyclic groups which satisfy the Huckel rule (i.e. they contain a carbocyclic ring system containing $2(2n+1)\pi$ electrons). Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions. Preferably an aryl group is an optionally substituted phenyl group.

Alkyl groups may be straight chain or branched. Thus, for example, a $C_4$ alkyl group could be n-butyl, i-butyl or t-butyl.

Alkylene groups are alkyl bi-radicals. Examples include —$CH_2$— and —$CH_2CH_2$—. A C1-alkylene group may be —$CH_2$— or —CHMe—.

Organic solvents include but are not limited to acetonitrile, ethers (e.g. tetrahydrofuran, 1,4-dioxane, diethyl ether, methyl-tert-butyl ether); ketones (e.g. acetone and methyl isobutyl ketone); halogenated solvents (e.g. dichloromethane, chloroform and 1,2-dichloroethane); and amides (e.g. DMF, NMP); or mixtures thereof.

Where step d) of the first aspect is conducted in the present of a nitrogen base, the organic solvent is most preferably a halogenated solvent or an amide.

Step d) is typically conducted at a suitable temperature, e.g. from about −5° C. to about 40° C. Preferably, the reaction temperature is about 25° C. to about 30° C. The reaction may be allowed to stir for a period of time from about 15 mins to about 16 h and preferably from about 30 mins to about 60 mins.

The processes of the invention may also involve deprotection of the hydroxy protecting groups.

It may be that the deprotection step (step b) is carried out without purifying the product of step a). It may be that the deprotection step (step e) is carried out without purifying the product of step d).

Where a protecting group is acid labile (e.g. trityl, C(O)OtBu, MOM, MEM, 2,4-dimethoxybenzyl, 2,3-dimethoxybenzyl, —$C(Me)_2$-) the deprotection step can be conducted using a suitable acid. The acid may be a Bronsted acid (e.g. TFA, phosphoric acid, HCl, or formic acid) or a Lewis acid (e.g. $ZnBr_2$, $CeCl_3$). Lewis acids (e.g. $ZnBr_2$) are less preferred. HCl is likewise less preferred. Preferably, the acid is TFA.

Where a protecting group is base sensitive, e.g. acetyl, benzoyl, 4-chlorobenzoyl, the deprotection step can be conducted using a suitable base, e.g. aqueous $NH_3$, methanolic ammonia solution, aqueous NaOH. Base sensitive groups may be less preferred for $R^6$.

Where a protecting group is a silyl group (e.g. triethylsilyl or t-butyldimethylsilyl), the deprotection step can be conducted using a suitable acid (e,g, TFA) or using a suitable fluoride source (e.g. tetrabutylammonium fluoride, fluorosilicic acid, HF).

Where a protecting group is a benzyl group or a C(O)Obenzyl group, the deprotection step can be conducted using $H_2$ and a suitable catalyst (e.g. Pd/C). Such protecting groups may be less preferred.

Where a protecting group is a 4-methoxybenzyl, 2,3-dimethoxybenzyl, 2,4-dimethoxybenzyl or C(O)O-(4-methoxybenzyl) the deprotection step can be performed using a suitable oxidizing agent (e.g. meta-chloroperbenzoic acid).

Where a protecting group is —C(O)—O-allyl, the deprotection step can be performed using $(PPh_3)_4Pd$ and an appropriate nucleophilic scavenger for the allylic cation such as $NaBH_4$ or N,N-dimethylbarbituric acid.

Where a protecting group is —C(O)—O—$CH_2$-fluorenyl, the deprotection step can be performed using piperidine.

The deprotection step may be conducted in an organic solvent or a mixture thereof. Exemplary organic solvents include, but are not limited to halogenated solvents (e.g. dichloromethane, chloroform, 1,2-dichloroethane); alcohols (e.g. methanol, ethanol, isopropanol) and ethers (e.g. tetrahydrofuran, diethyl ether).

Where the deprotection step is carried out in the presence of an acid (e.g. TFA), the organic solvent is preferably a halogenated solvent, e.g. dichloromethane.

The deprotection reaction may be carried out at a temperature in the range of, for example −10° C. to about 30° C., e.g. to about 10° C. A convenient temperature to carry out the reaction is −5° C. to 5° C. The reaction may be allowed to stir for a period of time from about 15 mins to about 16 hours and preferably from about 1 hour to about 4 hours, and more preferably from about 2 hours to about 3 hours.

Where, the deprotection is performed in the presence of an acid (e.g. TFA), isolation of the product obtained after the deprotection is typically done by quenching the excess acid used in deprotection step with an appropriate base, and extracting the product with a water immiscible organic solvent and recovering the product by evaporation of the organic solvent.

Examples of water immiscible organic solvents useful in extraction include esters such as ethyl acetate, methyl acetate, isopropyl acetate and the like; chlorinated solvents such as dichloromethane, chloroform and the like; aromatic hydrocarbon solvents such as toluene, xylene and the like; preferably ethyl acetate.

In certain embodiments, it may still be desirable to purify product of any and all reaction steps. Methods of purification are well known to those skilled in the art and include chromatography (e.g. column chromatography), recrystallisation and distillation. In other embodiments, no purification is necessary.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

The following abbreviations are used throughout this specification:

EXAMPLES

The present invention is further illustrated by the following examples, which are provided by way of illustration only and should not be construed to limit the scope of the invention.

Example 1: Preparation of 3',5'-di-O-(4-chlorobenzoyl)-5-fluoro-2'-β-deoxyuridine 3 (An Illustrative Example of a Compound of Formula IIIa)

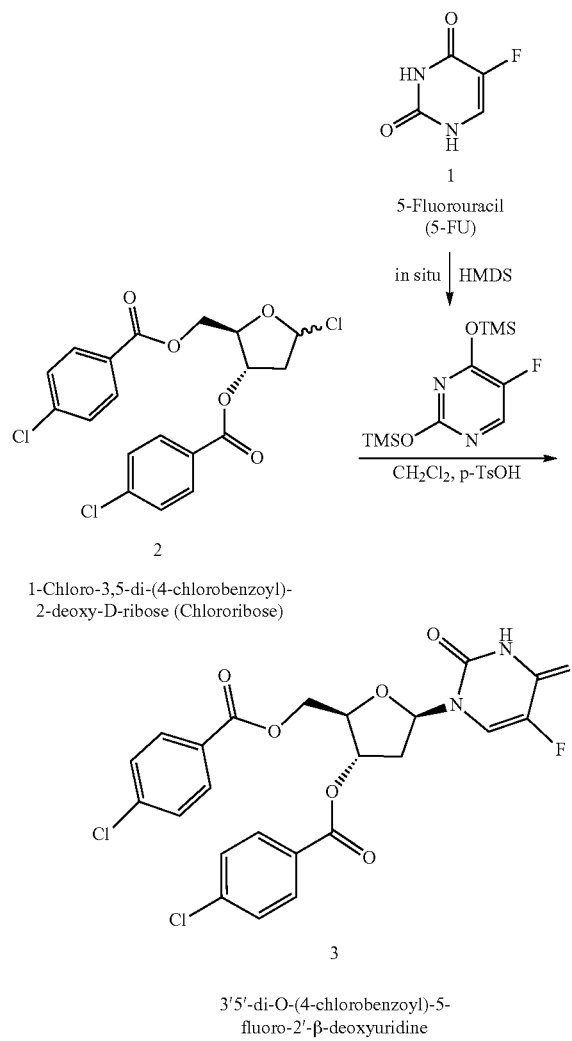

In a 1 L vessel at 30° C. was added bis(trimethylsilyl) amine [HMDS] (100 mL, 2 v/w with respect to 1), 5-Fluorouracil 1 (16.65 g, 0.128 moles) and then stirred for 10-20 minutes. The reaction mixture was then heated to 120° C. for 4-6 hr after which it was cooled to 75° C. and any unreacted HMDS was removed under vacuum (600 mmHg, 75° C.). The reaction was then azeotroped by cooling the vessel to 35° C., adding chlorobenzene (100 mL, 2 v/w) which was then distilled under vacuum (600 mmHg, 75° C.); this procedure was repeated twice. The reaction mass was cooled to 25° C., $CH_2Cl_2$ (225 ml., 4 v/w of the preceding mass) was added, and then the reaction was cooled to 5° C. 1-Chloro-3,5-di-(4-chlorobenzoyl)-2-deoxy-d-ribose 2 (50 g, 0.0582 mol is 25 g 0.1168 mol is 50 g) and more $CH_2Cl_2$ (25 mL, 0.5 v/w) was added and the reaction mixture was stirred for 15-30 min at 5° C. p-Toluene sulfonic acid monohydrate (2.214 g, 0.01164 moles) was added at 5° C., the temperature was raised to 12±3° C. and subsequently stirred for 20-24 h (if the temperature increases above 15° C. the proportion of the α-anomer increases).

Once the reaction was complete, as determined by HPLC, it was transferred into a 2 L flask containing isopropanol ($^i$PrOH) (250 mL, 5 v/w) at 25° C., using an additional $^i$PrOH (500 mL) to aid transfer. The reaction slurry was stirred for 2-3 h at 25° C. after which it was filtered under vacuum and washed with $^i$PrOH (100 mL at 25° C.). The moist filter cake was recrystallized from acetic acid (750 mL, 15 v/w) at 80° C. by cooling to 25° C. gradually over 2 h. The reaction mixture was stirred for an additional 2-3 h at 25° C., then filtered and washed with acetic acid (100 mL, 2 v/w), $^i$PrOH (100 mL, 2 v/w), and dried under vacuum at 55° C. to give 3:

Output:
Wt. of the compound 3: 38.5 g
Yield: 63
HPLC purity: 99.49% (α-anomer 0.1%)
Characterisation data for 3 is consistent with that which has been previously reported in Aoyama et al. (Bull. Chem. Soc. Jpn., 1987, 60, 2073-2077).

Example 2: Preparation of T-Deoxy-5-fluorouridine (FUDR)

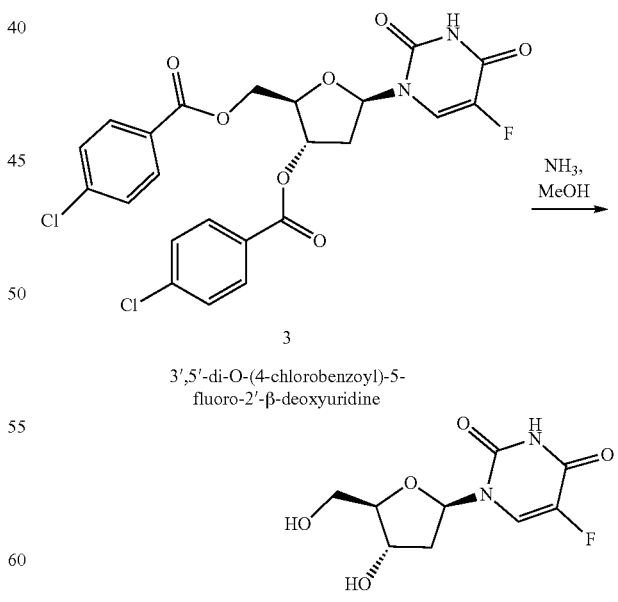

To a solution of methanolic ammonia (10-12% w/w; 500 mL, 10 v/w) at 10° C. was added 3',5'-di-O-(4-chlorobenzoyl)-5-fluoro-2'-β-deoxyuridine 3 (50 g, 0.0955 mole). The reaction mixture was raised to 25° C. over 1-2 h and maintained at this temperature for 20-24 h. When the reaction was complete, as determined by HPLC, it was filtered through Celite® at 25° C. The Celite® was washed with MeOH (100 mL, 2 v/w) and the combined filtrate was concentrated to between 50-100 mL under vacuum (600 mmHg, <45° C.). Ethyl acetate was added (100 mL, 2 v/w), then concentrated under vacuum to approximately 50-100 mL. More ethyl acetate (350 mL, 7 v/w) was added and the resulting slurry was maintained at 30° C. for 2-3 h. The reaction slurry was then filtered under vacuum and washed with ethyl acetate (100 mL, 2 v/w). The resulting solid was triturated with ethyl acetate (150 mL, 3 v) at 30° C., filtered under vacuum, washed with more with ethyl acetate (100 mL, 2 v/w) and dried under vacuum to obtain FUDR as solid:

Output:
Wt. of the compound FUDR: 20.2 g
Yield: 86.2%
HPLC Purity: 99.94%

Characterisation data for FUDR is consistent with that which has been previously reported, e.g. in Aoyama et al. (Bull. Chem. Soc. Jpn., 1987, 60, 2073-2077).

Example 3: Preparation of Diastereoisomeric Mixture of 2-[(2,3,4,5,6-pentafluorophenoxy)-naphth-1-oxy-phosphoryl amino] ppropionic Acid Benzyl Ester 9 (an Illustrative Example of a Compound of Formula IVb)

maintaining the temperature at below −70° C. and the mixture was stirred for 1 h at −70° C. The mixture was warmed to 25° C. and stirred for 1 h before being cooled to −50° C. L-alanine benzyl ester 6 (HCl salt; 1 eq.) was added to the mixture which stirred for 10 min before triethylamine (2.2 eq) in DCM (200 mL) was added at −50° C. over 30 minutes. The mixture was stirred for 1 h at −50° C. before being warmed to 25° C. and stirred for a further 1 h. The mixture was cooled to −10° C. and stirred for 10 min before pentafluorophenol 8 in DCM (200 mL) was added to the reaction mass slowly at below −10° C. The mixture was stirred at −10° C. for 10 min before triethylamine (1.1 eq.) was added over 30 min at −10° C. The mixture was stirred at −10° C. for 1 h before the mixture was warmed to 0° C. Water (1 L) was added and the mixture was stirred for 30 min at 0° C. The mixture was warmed to 25° C. and stirred for 5-10 min before the organic layer was separated. The aqueous layer was extracted with DCM (500 mL). The combined organic layers were washed with 7% sodium bicarbonate solution (2×1 L) and the organic layer was dried over anhydrous sodium sulphate before being concentrated in vacuo.

50% IPA/water (2.4 L) was added to the crude compound and stirred for 1 h at 25° C. The solid compound was filtered and the wet cake was washed with 50% IPA/water (500 mL) before being dried in vacuo. Again 50% IPA/water (2.4 L) was added to the crude compound and stirred for 1 h at 25° C. before being filtered and the wet cake was again washed with 50% IPA/water (500 mL) before being dried in vacuo.

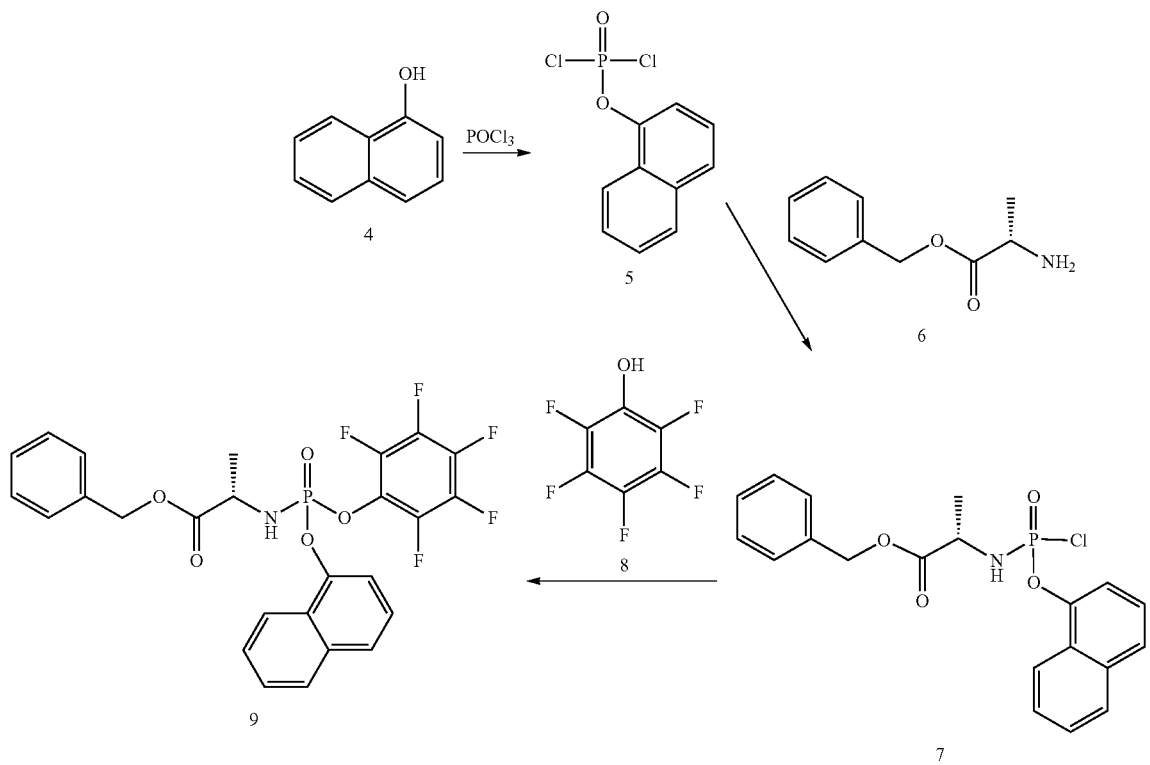

Alpha-naphthol 4 (100 g) was dissolved in DCM (1 L) at 25° C. and POCl₃ (1.1 eq) was added at 25° C. and stirred for 10 min before the mixture was cooled to −70° C. and stirred for 10 min. Triethylamine (1.1 eq.) was added slowly The semi-dried compound was washed with cyclohexane (10 v/w) at 25-30° C. for 1 h before the solid compound was washed with cyclohexane (2 L) and the wet compound 9 was dried under vacuum at 55-60° C. ° C. for 12 h Results:

Weight of the compound 9: 252 g

Overall yield: 66

HPLC purity: 98.31% (diastereoisomeric ratio is 1:1)

$^{31}$P NMR (202 MHz, CDCl$_3$): $\delta_P$ −1.35, −1.41; $^1$H NMR (500 MHz, CDCl$_3$): $\delta_H$ 8.13-8.10 (1H, m, H—Ar), 7.90-7.88 (1H, m, H—Ar), 7.73 (1H, apparent d, J=8.5 Hz, H—Ar), 7.62-7.55 (3H, m, H—Ar), 7.45-7.41 (1H, m, H—Ar), 7.36-7.28 (5H, m, H—Ar), 5.01 (1H, apparent s, CH$_2$Ph), 5.12 (1H, q, J=12.5 Hz, CH$_2$Ph), 4.38-4.31 (1H, m, NHCHCH$_3$), 4.17-4.08 (1H, m, NHCHCH$_3$), 1.49, 1.47 (3H, 2×d, J=3.5 Hz, NHCHCH$_3$); MS (ES+) m/z: 574 (M+Na$^+$, 100%), Accurate mass: C$_{26}$H$_{19}$F$_5$NO$_5$P required 551.40 found 574.05 (M+Na$^+$; Reverse-phase HPLC, eluting with H$_2$O/MeOH in 20/80 in 35 min, F=1 mL/min, $\lambda$=254, two peaks for two diastereoisomers with $t_R$=12.96, 14.48 min.

The diastereoisomers of compound 9 were separated by HPLC with Biotage Isolera using C18 SNAP Ultra (30 g) cartridge with a mixture of MeOH/H$_2$O (70%/30%) as an eluent to give: the fast eluting isomer (believed to be the Rp diastereoisomer) and the slow eluting isomer (believed to be the Sp diastereoisomer)

Note: Isomers are named as fast eluting (FE) and slow eluting (SE) based on retention time on C18 (reversed phase) cartridge and HPLC analytical column.

Fast eluting isomer (believed to be the Rp diastereoisomer): $^{31}$P NMR (202 MHz, CDCl$_3$): $\delta_P$−1.41; $^1$H NMR (500 MHz, CDCl$_3$): $\delta_H$ 8.02 (1H, dd, J=7.0, 2.0 Hz, H—Ar), 7.79 (1H, dd, J=6.5, 3.0 Hz, H—Ar), 7.64 (1H, d, J=8.5 Hz, H—Ar), 7.53-7.45 (3H, m, H—Ar), 7.33 (1H, t, J=8.0 Hz, H—Ar), 7.28-7.23 (5H, m, H—Ar), 5.09 (s, 2H, CH$_2$Ph), 4.29-4.21 (1H, m, NHCHCH$_3$), 4.02-3.97 (1H, m, NHCHCH$_3$), 1.38 (3H, d, J=7.0 Hz, NHCHCH$_3$); MS (ES+) m/z: MS (ES+) m/z: 574 (M+Na$^+$, 100%), Accurate mass: C$_{26}$H$_{19}$F$_5$NO$_5$P required 551.40 found 574.05 (M+Na$^+$; Reverse-phase HPLC, eluting with H$_2$O/MeOH in 20/80 in 35 min, F=1 mL/min, $\lambda$=254, $t_R$=12.96.

Slow eluting isomer (believed to be the Sp diastereoisomer): $^{31}$P NMR (202 MHz, CDCl$_3$): $\delta_P$−1.36; $^1$H NMR (500 MHz, CDCl$_3$): $\delta_H$ 8.14-8.11 (1H, m, H—Ar), 7.90-7.87 (1H, m, H—Ar), 7.74 (1H, d, J=8.0 Hz, H—Ar), 7.60 (1H, d, J=8.0 Hz, H—Ar), 7.58-7.55 (2H, m, H—Ar), 7.44 (1H, t, J=8.0 Hz, H—Ar), 7.34-7.30 (5H, m, H—Ar), 5.12 (2H, q, J=12.5 Hz, CH$_2$Ph), 4.35-4.29 (1H, m, NHCHCH$_3$), 4.04-4.00 (1H, m, NHCHCH$_3$), 1.48 (3H, d, J=7.0 Hz, NHCHCH$_3$); MS (ES+) m/z: MS (ES+) m/z: 574 (M+Na$^+$, 100%), Accurate mass: C$_{26}$H$_{19}$F$_5$NO$_5$P required 551.40 found 574.05 (M+Na$^+$); Reverse-phase HPLC, eluting with H$_2$O/MeOH in 20/80 in 35 min, F=1 mL/min, $\lambda$=254, $t_R$=14.48.

Example 4: Enrichment of S$_p$-diastereoisomer of 2-[(2,3,4,5,6-pentafluorophenoxy)-naphth-1-oxy-phosphoryl amino] propionic acid benzyl ester (9) Sp-diastereoisomer

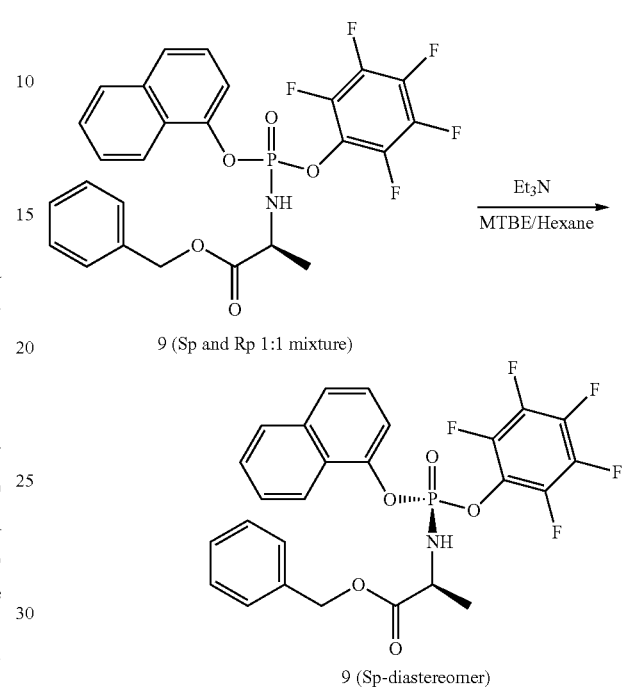

9 (Sp and Rp 1:1 mixture)

9 (Sp-diastereomer)

A 1:1 diastereoisomeric mixture of compound 9 (25 g) was dissolved in 10% MTBE/n-Hexane (500 mL) and triethylamine (2.5 mL) was added to the reaction mass at 25° C. The mixture was stirred for 80 h at 30° C. The mixture was filtered and the wet cake was washed with 10% MTBE/n-hexane (75 mL) before being dried in vacuo 30 min. 50% IPA/water (200 mL) was added to above crude compound and stirred for 1 h at 25-35° C. before being filtered. The wet cake was washed with 50% IPA/water (100 mL) before being dried in vacuo at 55-60° C. for 12 h to give XX in diastereo enriched form:

Output:

Wt. of the compound Sp-9: 17 g

Yield: 68

HPLC purity: 97.66

Slow eluting isomer (believed to be Sp-diastereoisomer): $^{31}$P NMR (202 MHz, CDCl$_3$): $\delta_P$−1.36; $^1$H NMR (500 MHz, CDCl$_3$): $\delta_H$ 8.14-8.11 (1H, m, H—Ar), 7.90-7.87 (1H, m, H—Ar), 7.74 (1H, d, J=8.0 Hz, H—Ar), 7.60 (1H, d, J=8.0 Hz, H—Ar), 7.58-7.55 (2H, m, H—Ar), 7.44 (1H, t, J=8.0 Hz, H—Ar), 7.34-7.30 (5H, m, H—Ar), 5.12 (2H, q, J=12.5 Hz, CH$_2$Ph), 4.35-4.29 (1H, m, NHCHCH$_3$), 4.04-4.00 (1H, m, NHCHCH$_3$), 1.48 (3H, d, J=7.0 Hz, NHCHCH$_3$); MS (ES+) m/z: MS (ES+) m/z: 574 (M+Na$^+$, 100%), Accurate mass: C$_{26}$H$_{19}$F$_5$NO$_5$P required 551.40 found 574.05 (M+Na$^+$); Reverse-phase HPLC, eluting with H$_2$O/MeOH in 20/80 in 35 min, F=1 mL/min, $\lambda$=254, $t_R$=14.48.

The stereochemistry (Rp vs Sp) of the two compound 9 isomers described above has been tentatively assigned on the basis of comparison of $^{31}$P chemical shift, $^1$H NMR spectra, and HPLC retention times of the NUC-3373 isomers made using the compound 9 isomers with those of other ProTides known in the literature. As mentioned above, the stereochemistry of the phosphate stereocentre is inverted during the process of the invention so the (S)-diastereoisomer of compound 9 will form the (S)-diastereoisomer of NUC-3373 and likewise the (R)-diastereoisomer of compound 9 will form the (R)-diastereoisomer of NUC-3373. The stereochemical assignment is supported by powder X-ray diffraction and differential scanning calorimetry that has been carried out on the two compound 9 isomers, but this is not in itself definitive.

Example 5—Formation of Sp and Rp Isomers of NUC-3373

3'-BOC protected FUDR 12 (an illustrative example of a compound of formula Va) can be made according to the following scheme.

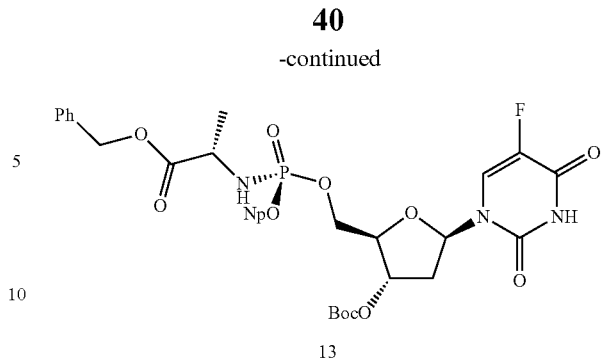

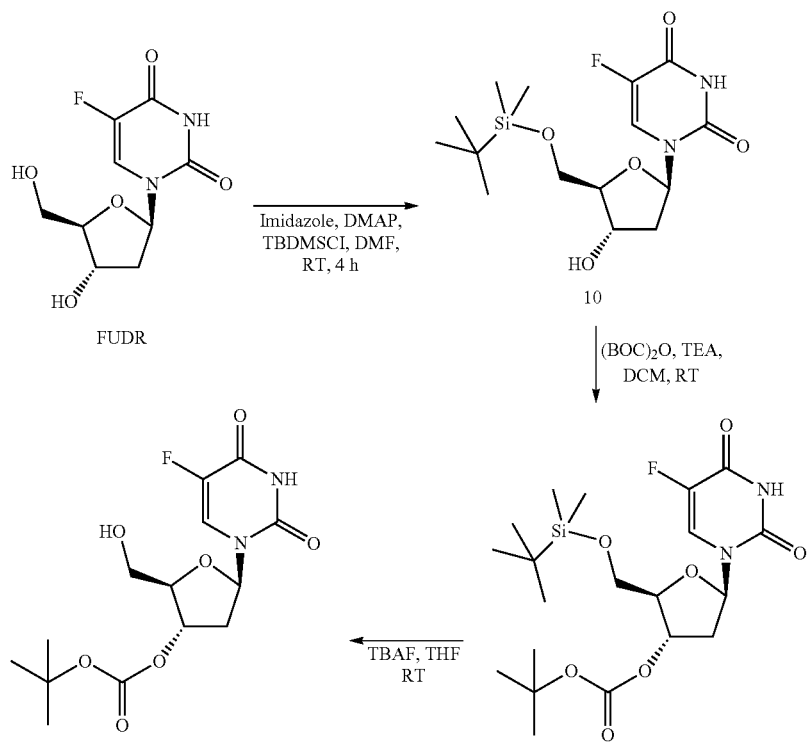

Compound 12 can then be coupled with a compound of formula IVb.

Example 6: Preparation of the Sp Isomer of Nuc-3373 from 12 and the Sp Isomer of Compound 9

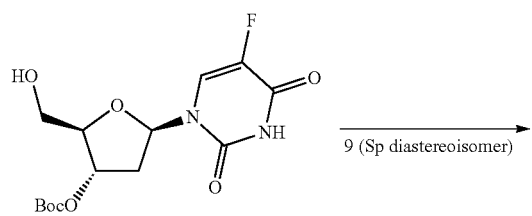

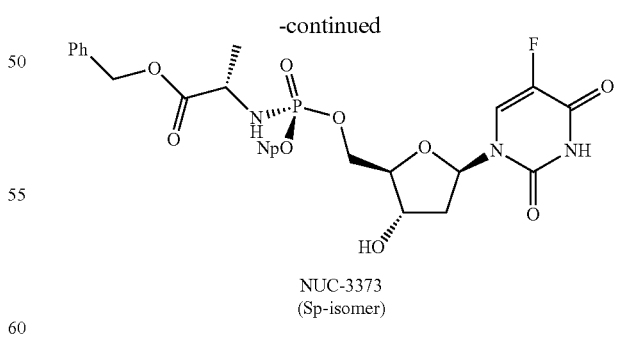

NUC-3373
(Sp-isomer)

Compound 12 (1 g) and the Sp isomer of compound 9 (1.2 eq) were dissolved in THF (10 mL) and the mixture was cooled to 0° C. t-Butyl magnesium chloride (2.5 eq., 2.0 M in THF) was added to the mixture over 15 min. The mixture was warmed and stirred at 25° C. for 4 h. The mixture was cooled to 10° C. and sat. ammonium chloride solution (10 mL) was added. Ethyl acetate (10 mL) was added to the mixture and the organic layer was separated. The aqueous layer was extracted with ethyl acetate (5 mL). The combined organic layers were washed with deionised water (5 mL) followed by 20% sodium chloride solution (5 mL). The organic layers were dried over anhydrous sodium sulphate before being concentrated in vacuo to provide 2.16 g of compound 13 (100% crude yield).

Crude compound 13 (1 g) was dissolved in DCM (5 mL) and cooled to 10° C. TFA (2 mL) was added slowly to the mixture, maintaining the temperature at below 20° C. The mixture was warmed to 30° C. and the stirred for 6 h. The mixture was cooled to 10° C. and deionized water (5 mL) was added slowly, maintaining the temperature at below 20° C. After stirring for 10 min the organic layer was separated and the aqueous layer was extracted with DCM (5 mL). The combined organic layers were washed with deionised water (2×5 mL), 7% sodium bicarbonate solution (2×5 mL) and 20% sodium chloride solution (5 mL) before being dried with anhydrous sodium sulphate (1 w/w) and concentrated in vacuo. Crude compound was purified with column chromatography in ethyl acetate/DCM using silica gel (100-200 mesh). Pure compound was eluted in 50% ethyl acetate/DCM to 100% ethyl acetate. The combined pure fractions were concentrated in vacuo before the compound slurry was washed with cyclohexane (5 mL) to give NUC-3373.

Output:
Weight of NUC-3373 (Sp isomer): 9.3 g
Overall yield: 70%
HPLC purity: 96.86%

$^1$H-NMR (500 MHz, MeOD): $\delta_H$ 8.16-8.14 (m, 1H, H—Ar), 7.90-7.80 (m, 1H, H—Ar), 7.72-7.70 (m, 2H, H—Ar), 7.54-7.49 (m, 3H, H—Ar, H-6), 7.43 (apparent t, 1H, J=8.0 Hz, H—Ar), 7.35-7.27 (m, 5H, H—Ar), 6.16-6.13 (m, 1H, H-1'), 5.11 (AB system, J=12.0 Hz, 2H, OCH$_2$Ph), 4.35-4.33 (m, 2H, 2×H-5'), 4.30-4.28 (m, 1H, H-3'), 4.14-4.08 (m, H, CHCH$_3$), 4.07-4.04 (m, 1H, H-4'), 2.14-2.09 (m, 1H, H-2'), 1.74-1.68 (m, 1H, H-2'), 1.35 (d, J=7.0 Hz, 3H, CHCH$_3$);

$^{13}$C-NMR (125 MHz, MeOD): $\delta_C$ 174.92 (d, $^3J_{C\text{-}P}$=3.75 Hz, C=O, ester), 159.37 (d, $^2J_{C\text{-}F}$=25.9 Hz, C=O, base), 150.54 (d, $^4J_{C\text{-}P}$=4.0 Hz, C=O, base), 147.99 (d, $^2J_{C\text{-}P}$=7.1 Hz, C—Ar, Naph), 141.75 (d, $^1J_{C\text{-}F}$=232.1 Hz, CF-base), 137.18, 136.29 (C—Ar), 129.59, 129.36, 128.90, 127.91 (CH—Ar), 127.83 (d, $^3J_{C\text{-}P}$=5.4 Hz, C—Ar, Naph), 127.59, 126.52, 126.50, 126.18 (CH—Ar), 125.54 (d, $^2J_{C\text{-}F}$=34.1 Hz, CH-base), 122.64 (CH—Ar), 116.29 (d, $^3J_{C\text{-}P}$=2.75 Hz, CH—Ar, Naph), 86.95 (C-1'), 86.67 (d, $^3J_{C\text{-}P}$=8.1 Hz, C-4'), 72.12 (C-3'), 68.05 (OCH$_2$Ph), 67.85 (d, $^2J_{C\text{-}P}$=5.3 Hz, C-5'), 51.96 (CHCH$_3$), 40.84 (C-2'), 20.52 (d, $^3J_{C\text{-}P}$=7.5 Hz, CHCH$_3$).

$^{31}$P-NMR (202 MHz, MeOD): $\delta_P$ 4.62;
$^{19}$F NMR (470 MHz, MeOD): $\delta_F$ −167.19;
(ES+) m/z Found: (M+Na$^+$) 636.1520. C$_{29}$H$_{29}$N$_3$O$_9$FNaP required: (M$^+$), 613.15. Reverse HPLC (Varian Pursuit XRs 5 C18, 150×4.6 mm) eluting with (H$_2$O/AcCN from 90/10 to 0/100) in 35 min., $t_R$ 16.61 min.

The Rp isomer of NUC-3373 can be accessed by performing the above process but starting with the Rp diastereoisomer of compound 9:

$^1$H-NMR (500 MHz, MeOD): $\delta_H$ 8.17-8.15 (m, 1H, H—Ar), 7.91-7.88 (m, 1H, H—Ar), 7.72-7.69 (m, 2H, H—Ar), 7.56-7.52 (m, 2H, H—Ar, H-6), 7.50-7.48 (m, 1H, H—Ar), 7.39 (apparent t, J=8.0 Hz, 1H, H—Ar), 7.35-7.28 (m, 5H, H—Ar), 6.16-6.09 (m, 1H, H-1'), 5.13 (s, 2H, OCH$_2$Ph), 4.35-4.25 (m, 3H, 2×H-5', H-3'), 4.14-4.08 (m, 1H, CHCH$_3$), 4.05-4.03 (m, 1H, H-4'), 2.15-2.10 (m, 1H, H-2'), 1.74-1.68 (m, 1H, H-2'), 1.36 (d, J=7.0 Hz, 3H, CHCH$_3$);

$^{13}$C-NMR (125 MHz, MeOD): $\delta_C$ 174.58 (d, $^3J_{C\text{-}P}$=5.0 Hz, C=O, ester), 159.38 (d, $^2J_{C\text{-}F}$=26.3 Hz, C=O), 150.48 (C=O base), 147.80 (d, $^2J_{C\text{-}P}$=6.5 Hz, C—Ar, Naph), 141.67 (d, $^1J_{C\text{-}F}$=232.5 Hz, CF-base), 137.15, 136.26 (C—Ar), 129.62, 129.40, 129.36, 128.96, 127.89 (CH—Ar), 127.84 (d, $^3J_{C\text{-}P}$=5.5 Hz, C—Ar, Naph), 127.59, 126.57, 126.55, 126.21 (CH—Ar), 125.61 (d, $^2J_{C\text{-}F}$=34.0 Hz, CH-base), 122.62 (CH—Ar), 116.55 (d, $^3J_{C\text{-}P}$=3.75 Hz, CH—Ar, Naph), 86.97 (C-1'), 86.66 (d, $^3J_{C\text{-}P}$=7.5 Hz, C-4'), 72.01 (C-3'), 68.07 (OCH$_2$Ph), 67.84 (d, $^2J_{C\text{-}P}$=5.0 Hz, C-5'), 51.83 (CHCH$_3$), 40.89 (C-2'), 20.42 (d, $^3J_{C\text{-}P}$=7.5 Hz, CHCH$_3$).

$^{31}$P-NMR (202 MHz, MeOD): $\delta_P$ 4.27;
$^{19}$F NMR (470 MHz, MeOD): $\delta_F$ −167.27;
(ES+) m/z Found: (M+Na$^+$) 636.1520. C$_{29}$H$_{29}$N$_3$O$_9$FNaP required: (M$^+$), 613.15.

Reverse HPLC (Varian Pursuit XRs 5 C18, 150×4.6 mm) eluting with (H$_2$O/MeOH from 90/10 to 0/100) in 35 min., $t_R$ 16.03 min.

The stereochemistry (Rp vs. Sp) of the two NUC-3373 isomers described above has been tentatively assigned on the basis of comparison of $^{31}$P chemical shift, $^1$H NMR spectra, and HPLC retention times with those of other ProTides known in the literature. The stereochemistry of compound 9 has been tentatively assigned based on which isomer of NUC-3373 that isomer of compound 9 forms.

What is claimed is:
1. A process for the preparation of FUDR in substantially diastereoisomerically pure form:

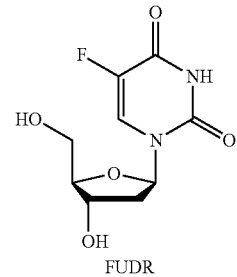
FUDR the process comprising step a) and optionally step b):
a) reacting a compound of Formula Ia with a compound of Formula IIa in the presence of a sulfonic or carboxylic acid A1 to provide a compound of Formula IIIa in substantially diastereomerically pure form:

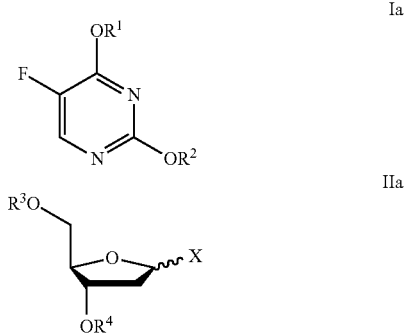

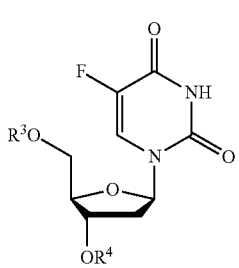

Formula IIIa wherein $R^1$ and $R^2$ are each independently trialkylsilyl groups; $R^3$ and $R^4$ are each independently selected from H and a protecting group; and X is a leaving group;
b) where $R^3$ and/or $R^4$ are protecting groups, optionally removing the protecting group $R^3$ and/or $R^4$ from the compound of formula IIIa to provide FUDR in substantially diastereomerically pure form;
wherein the step of reacting a compound of Formula Ia with a compound of Formula IIa is carried out at a temperature T1 in the range from 9° C. to 15° C., in a solvent S1.

2. The process of claim 1, wherein the step of reacting a compound of Formula Ia with a compound of Formula IIa is carried out in a solvent S1 selected from acetonitrile, 1,2-dichloroethane and dichloromethane.

3. The process of claim 1, wherein the acid A1 is a sulfonic acid.

4. The process of claim 3, wherein the sulfonic acid is selected from the group consisting of camphorsulfonic acid, benzenesulfonic acid, p-toluenesulfonic acid, and methanesulfonic acid.

5. The process of claim 4, wherein the acid A1 is p-toluenesulfonic acid.

6. The process of claim 1, wherein the step of reacting a compound of Formula Ia with a compound of Formula IIa is carried out in a solvent S1 that is dichloromethane.

7. The process of claim 1, wherein R1 and R2 are each trimethylsilyl.

8. The process of claim 1, wherein R3 and R4 are each a 4-chlorobenzoyl group.

9. The process of claim 8, wherein R3 and R4 are removed using methanolic ammonia solution.

10. The process of claim 1, wherein X is Cl.

11. The process of claim 1, wherein the process further comprises converting the FUDR to NUC-3373:

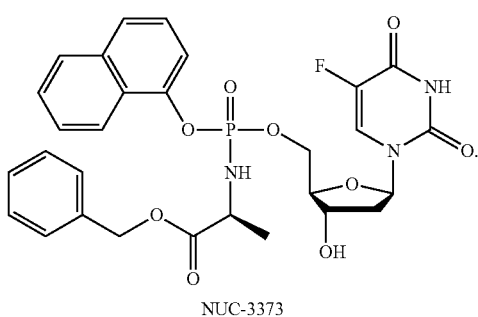

NUC-3373

12. The process of claim 11, wherein the FUDR is converted to NUC-3373 in a process comprising step d) and optionally comprising steps c) and e):

c) optionally converting FUDR to a compound of formula Va in which $R^6$ is a protecting group;
d) reacting a compound of Formula IVa; with a compound of Formula Va in presence of a base (B2) to provide a compound of Formula VIa; wherein $R^5$ is a leaving group, and $R^6$ is independently selected from H (in which case the compound of formula Va is FUDR) and a protecting group:

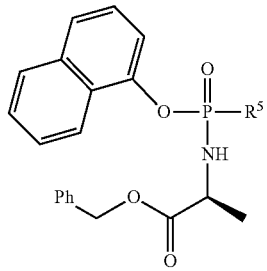

Formula IVa

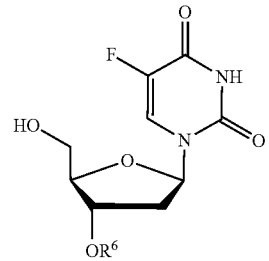

Formula Va

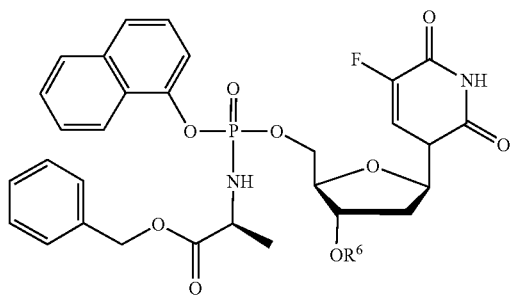

Formula VIa e) where $R^6$ is a protecting group, optionally removing the protecting group $R^6$ from the compound of formula VIa to provide NUC-3373.

13. The process of claim 12, wherein R6 is a carbonate protecting group.

14. The process of claim 12, wherein R6 is selected from the group consisting of a silyl protecting group, carbonate protecting group, benzyl protecting group, an optionally substituted —C(aryl)$_3$, and —C$_1$—C$_2$alkyl-O—C$_1$—C$_4$-alkyl.

15. The process of claim 14, wherein R6 is an ester protecting group.

16. The process of claim 14, wherein R6 is a silyl protecting group.

17. The process of claim 14, wherein R6 is a carbonate protecting group.

18. The process of claim 1, wherein the acid A1 is a carboxylic acid.

19. The process of claim 1, wherein R3 and R4 are independently selected from the group consisting of a silyl protecting group, ester, carbonate protecting group, benzyl protecting group, an optionally substituted —C(aryl)$_3$, and —C$_1$—C$_2$alkyl-O—C$_1$—C$_4$-alkyl.

20. The process of claim 19, wherein R3 is an ester protecting group.

21. The process of claim 20, wherein the ester protecting group is a benzoyl group;
optionally substituted where chemically possible, by 1 to 3 substituents which are each independently at each occurrence selected from the group consisting of: halo, nitro, cyano, NR$^a$R$^a$, NR$^a$S(O)$_2$R$^a$, NR$^a$CONR$^a$R$^a$, NR$^a$CO$_2$R$^a$, OR$^a$, SR$^a$, SOR$^a$, SO$_3$R$^a$, SO$_2$R$^a$, SO$_2$NR$^a$R$^a$, CO2R$^a$C(O)R$^a$, CONR$^a$R$^a$, C$_1$-C$_4$-alkyl, C$_2$-C$_4$-alkenyl, and C$_1$-C$_4$ haloalkyl;
wherein R$^o$ is independently at each occurrence selected from H, C$_1$-C$_4$ alkyl and C$_1$-C$_4$ haloalkyl.

22. The process of claim 21, wherein the ester protecting group is 4-chlorobenzoyl.

23. The process of claim 19, wherein R4 is an ester protecting group.

24. The process of claim 23, wherein the ester protecting group is a benzoyl group, optionally substituted where chemically possible, by 1 to 3 substituents which are each independently at each occurrence selected from the group consisting of: halo, nitro, cyano, NR$^a$R$^a$, NR$^a$S(O)$_2$R$^a$, NR$^a$CONR$^a$R$^a$, NR$^a$CO$_2$R$^a$, OR$^a$, SR$^a$, SOR$^a$, SO$_3$R$^a$, SO$_2$R$^a$, SO$_2$NR$^a$R$^a$, CO2R$^a$C(O)R$^a$, CONR$^a$R$^a$, C$_1$-C$_4$-alkyl, C$_2$-C$_4$-alkenyl, and C$_1$-C$_4$ haloalkyl;
wherein R$^o$ is independently at each occurrence selected from H, C$_1$-C$_4$ alkyl and C$_1$-C$_4$ haloalkyl.

25. The process of claim 24, wherein the ester protecting group is 4-chlorobenzoyl.

26. The process of claim 19, wherein R3 is a silyl protecting group.

27. The process of claim 19, wherein R4 is a silyl protecting group.

28. The process of claim 19, wherein R3 is a carbonate protecting group.

29. The process of claim 19, wherein R4 is a carbonate protecting group.

30. The process of claim 1, wherein the leaving group X is selected from the group consisting of halo, OC(O)—C$_1$—C$_4$-alykl, O—C$_1$—C$_4$ alkyl, and OH.

31. The process of claim 30, wherein X is halo.

32. The process of claim 12, wherein R5 is selected from the group consisting of halo, sulfonate, or phenolic leaving group substituted with from 1 to 5 R7 groups, wherein each R7 group is independently selected from the group consisting of fluoro, chloro, bromo, iodo, trifluoromethyl, cyano, and nitro.

* * * * *